US007811984B2

(12) United States Patent
Ferrara et al.

(10) Patent No.: US 7,811,984 B2
(45) Date of Patent: *Oct. 12, 2010

(54) BV8 NUCLEIC ACIDS AND POLYPEPTIDES WITH MITOGENIC ACTIVITY

(75) Inventors: Napoleone Ferrara, San Francisco, CA (US); Jennifer Le Couter, San Francisco, CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/536,880

(22) Filed: Sep. 29, 2006

(65) Prior Publication Data

US 2007/0244063 A1    Oct. 18, 2007

Related U.S. Application Data

(63) Continuation of application No. 11/384,222, filed on Mar. 17, 2006, which is a continuation of application No. 10/231,411, filed on Aug. 27, 2002, now Pat. No. 7,060,278.

(60) Provisional application No. 60/316,184, filed on Aug. 29, 2001.

(51) Int. Cl.
    *A61K 38/00* (2006.01)
(52) U.S. Cl. .......................................... 514/2; 530/350
(58) Field of Classification Search .................. 514/2; 530/350
    See application file for complete search history.

(56) References Cited

U.S. PATENT DOCUMENTS

| | | | |
|---|---|---|---|
| 4,109,496 A | 8/1978 | Allemann et al. |
| 4,419,446 A | 12/1983 | Howley et al. |
| 4,601,978 A | 7/1986 | Karin |
| 5,010,182 A | 4/1991 | Brake et al. |
| 5,240,848 A | 8/1993 | Keck et al. |
| 5,332,671 A | 7/1994 | Ferrara et al. |
| 5,364,934 A | 11/1994 | Drayna et al. |
| 5,561,053 A | 10/1996 | Crowley |
| 5,605,793 A | 2/1997 | Stemmer |
| 5,837,458 A | 11/1998 | Minshull et al. |
| 5,976,782 A | 11/1999 | Parish et al. |
| 7,060,278 B2 * | 6/2006 | Ferrara et al. |
| 2002/0172678 A1 | 11/2002 | Ferrara et al. |

FOREIGN PATENT DOCUMENTS

| | | |
|---|---|---|
| EP | 0 307 247 A2 | 3/1989 |
| EP | 0 362 179 A2 | 4/1990 |
| WO | WO 90/13646 | 11/1990 |
| WO | WO 91/08291 | 6/1991 |
| WO | WO 91/08298 | 6/1991 |
| WO | WO 98/10071 | 3/1998 |
| WO | WO 01/36465 A2 | 5/2001 |
| WO | WO 02/00711 | 1/2002 |
| WO | WO 02/36625 A2 | 5/2002 |
| WO | WO 2004/081229 | 9/2004 |

OTHER PUBLICATIONS

Nor et al (Angio., 3:101-116, 1999).*
Eming et al (Prog. Hist. Cyto., 42:115-170, 2007).*
Jones (Pharmacogenomics Journal, 1:126-134, 2001).*
Tosatto et al (Current Pharmaceutical Design, 12:2067-2086, 2006).*
Skolnick et al. (Trends in Biotechnology 2000; 18: 34-39).*
Guo et al. (Proc. Natl. Acad. Sci. USA. Jun. 22, 2004; 101 (25): 9205-9210).*
Ferrara et al (Biochim. Biophys. Acta., 1654:69-78:2004).*
Masuda et al (Biochem. Biophys. Res. Com., 293(1):396-402, 2002).*
Thiboutot et al (J. Invest. Derm. 120:905-914, 2003).*
Galiano et al (Am. J. Path., 164(6):1935-1947, 2004).*
Aird, W. et al., 1997, *The Journal of Cell Biology*, 138(5):1117-1124 "Vascular Bed-specific Expression of an Endothelial Cell Gene is Programmed by the Tissue Microenvironment".
Aravind, L. et al., 1998, *Current Biology*, 8(14):R477-R478 "A colipase fold in the carboxy-terminal domain of the Wnt antagonists—the Dickkopfs".
Aruffo, A. et al., 1990, *Cell*, 61:1303-1313 "CD44 is the Principal Cell Surface Receptor for Hyaluronate".
Ashkenazi, A. et al., 1993, *Intern. Rev. Immunol.*, 10:219-227 "Immunoadhesins".
Ashkenazi, A. et al., 1991, *Proc. Natl. Acad. Sci. USA*, 88:10535-10539 "Protection against endotoxic shock by a tumor necrosis factor receptor immunoadhesin".
Bianchi, M. et al., 1987, *Curr. Genet.*, 12:185-192 "Transformation of the yeast *Kluyveromyces lactis* by new vectors derived from the 1.6 μm circular plasmid pKD1".
Bowie et al., 1990, *Science*, 247" 1306-1310 "Deciphering the Message in Protein Sequences: Tolerance to Amino Substitutions".
Burgess et al., 1990, *Journal of Cell Biology*, 111:2129-2138 "Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue".
Carmeliet, P., 2000, *Nature Medicine*, 6(3):389-395 "Mechanisms of angiogenesis and arteriogenesis".
Carter, P. et al., 1985, *Nucleic Acids Research*, 13(12):4431-4443 "Improved oligonucleotide site-directed mutagenesis using M13 vectors".
Carter, P. et al., 1992, *Bio/Technology*, 10:163-167 "High Level *Escherichia coli* Expression and Production of a Bivalent Humanized Antibody Fragment".
Chothia, C. et al., 1987, *J. Mol. Biol.*, 196:901-917 "Canonical Structures for the Hypervariable Regions of Immunoglobulins".
Cunningham, B. et al., 1989, *Science*, 244:1081-1085 "High-Resolution Epitope Mapping of hGH-Receptor Interactions by Alanine-Scanning Mutagenesis".

(Continued)

*Primary Examiner*—Stephen L Rawlings
*Assistant Examiner*—Brad Duffy
(74) *Attorney, Agent, or Firm*—Jones Day

(57) ABSTRACT

The present invention provides methods of using Bv8 polypeptides to induce endothelial cell proliferation and to enhance endothelial cell survival. Also provided herein are methods of screening for modulators of Bv8 activity. Furthermore, methods of treatment using Bv8 polypeptides are provided.

6 Claims, 13 Drawing Sheets

OTHER PUBLICATIONS

Dellian, M. et al., 1996, *Amer. Journal of Pathology*, 149(1):59-71 "Quantitation and Physiological Characterization of Angiogenic Vessels in Mice".

Dietsch, M. et al., 1993, *Journal of Immunological Methods*, 162:123-132 "Bispecific receptor globulins, novel tools for the study of cellular interactions".

Dzau, V. et al., 1993, *Trends Biotechnol.*, 11:205-210 "Gene therapy for cardiovascular disease".

Ferrara, N. et al., 1999, *Nature Medicine*, 5(12):1359-1364 "Clinical applications of angiogenic growth factors and their inhibitors".

Fleer, R. et al., 1991, *Bio/Technology*, 9:968-975 "Stable Multicopy Vectors for High-Level Secretion of Recombinant Human Serum Albumin by *Kluyveromyces* Yeasts".

Gascoigne, N. et al., 1987, *PNAS USA*, 84:2936-2940 "Secretion of a chimeric T-cell receptor-immunoglobulin protein".

Gautier et al., 1987, *Nucleic Acids Research*, 15(16):6625-6641 "DNA IV: α-anomeric and β-anomeric tetrathymidylates covalently linked to intercalating oxazolopyridocarbazole. Synthesis, physicochemical properties and poly (rA) binding".

Hoogenboom, H. et al., 1991, *Molecular Immunology*, 28(9).1027-1037 "Construction and Expression of Antibody-Tumor Necrosis Factor Fusion Proteins".

Houghten, R. et al., 1991, *Nature*, 354:84-86 "Generation and use of synthetic peptide combinatorial libraries for basic research and drug discovery".

Inoue, H. et al., 1987, *FEBS Letters*, 215(2):327-330 "Sequence-dependent hydrolysis of RNA using modified oligonucleotide splints and RNase H".

Inoue, H. et al., 1987, *Nucleic Acids Research*, 15(15):6131-6148 "Synthesis and hybridization studies on two complementary nona(2'-O-methyl)ribonucieotides".

Keck, P. et al., 1989, *Science*, 246:1309-1312 "Vascular Permeability Factor, an Endothelial Cell Mitogen Related to PDGF".

Lam, K. et al., 1991, *Nature*, 354:82-84 "A new type of synthetic peptide library for identifying ligand-binding activity".

Lazar et al., 1988, *Molecular and Cellular Biology*, 8:1247-1252 "Transforming Growth Factor α: Mutation of Aspartic Acid 47 and Leucine 48 Results in Different Biological Activities".

LeCouter, J. et al., 2001, *Nature*, 412:877-884 "Identification of an angiogenic mitogen selective for endocrine gland endothelium".

LeCouter, J. et al., 2003, *PNAS*, 100(5):2685-2690 "The endocrine-gland-derived VEGF homologue Bv8 promotes angiogenesis in the testis: Localization of Bv8 receptors to endothelial cells".

Leung, D. et al., 1989, *Science*, 246:1306-1309 "Vascular Endothelial Growth Factor is a Secreted Angiogenic Mitogen".

Li, M. et al., 2001, *Molecular Pharm.*, 59(4):692-698 "Identification of Two Prokineticin cDNAs: Recombinant Proteins Potently Contract Gastrointestinal Smooth Muscle".

Lovell, D. et al., 2000, *The New England Journal of Medicine*, 342(11):763-769 "Etanercept in Children with Polyarticular Juvenile Rheumatoid Arthritis".

Maini, R. et al., 2000, *Annu. Rev. Med.*, 51:207-229 "Anti-Cytokine Therapy for Rheumatoid Arthritis".

Martin, S. et al., 1993, *Journal of Virology*, 67(6);3561-3568 "Efficient Neutralization and Disruption of Rhinovirus by Chimeric ICAM-I/Immunoglobulin Molecules".

Mollay, C. et al., 1999, *European Journal of Pharmacology*, 374:189-196 "Bv8, a small protein from frog skin and its homologue from snake venom induce hyperalgesia in rats".

Platt, K. et al., 1994, *The Journal of Biological Chemistry*, 269(46):28558-28562 "Independent Regulation of Adipose Tissue-specificity and Obesity Response of the Adipsin Promoter in Transgenic Mice".

Roberts, W. et al., 1998, *Amer. Journal of Pathology*, 153(4).1239-1248 "Host Microvasculature Influence on Tumor Vascular Morphology and Endothelial Gene Expression".

Schweitz, H. et al., 1999, *FEBS Letters*, 461:183-188 "$MIT_1$, a black mamba toxin with a new and highly potent activity on intestinal contraction".

Siebenlist, U. et al., 1980, *Cell*, 20:269-281 "*E. coli* RNA Polymerase Interacts Homologously with Two Different Promoters".

Simionescu, N. et al., 1988, *Cell and Tissue Biology—A Textbook of Histology*, 6th Ed, Ch 10, pp. 355-400 "The Cardiovascular System".

Songyang, Z. et al., 1993, *Cell*, V72:767-778 "SH2 Domains Recognize Specific Phosphopeptide Sequences".

Stamenkovic, I. et al., 1991, *Cell*, 66:1133-1144 "The B Lymphocyte Adhesion Molecule CD22 Interacts with Leukocyte Common Antigen CD45RO on T Cells and α2-6 Sialyltransferase, CD75, on B Cells".

Stewart, P. et al., 1981, *Developmental Biology*, 84(1):183-192 "Developing Nervous Tissue Induces Formation of Blood-Brain Barrier Characteristics in Invading Endothelial Cells: A Study Using Quail-Chick Transplantation Chimeras".

van den Berg, J. et al., 1990, *Bio/Technology*, 8:135-139 "*Kluyverontyces* as a Host for Heterologous Gene Expression: Expression and Secretion of Prochymosin".

Wechselberger, C. et al., 1999, *FEBS Letters*, 462:177-181 "The mammalian homologues of frog Bv8 are mainly expressed in spermatocytes".

Weinblatt, M. et al., 1999, *The New England Journal of Medicine*, 340(4):253-259 "A Trial of Etanercept, a Recombinant Tumor Necrosis Factor Receptor: Fc Fusion Protein, in Patients with Rheumatoid Arthritis Receiving Methotrexate".

Wells, J. et al., 1985, *Gene*, 34:315-323 "Cassette mutagenesis: an efficient method for generation of multiple mutations at defined sites".

Wells, J. et al., 1986, *Phil. Trans. R. Soc. Lond.*, Ser. A, 317:415-423 "Importance of hydrogen-bond formation in stabilizing the transition state of subtilisin".

Zamecnik, P. et al., 1986, *Proc. Natl. Acad. Sci. USA*, 83:4143-4146 "Inhibition of replication and expression of human T-cell lymphotropic virus type III in cultured cells by exogenous synthetic oligonucleotides complementary to viral RNA".

Zapata, G. et al., 1995, *Protein Engineering*, 8(10):1057-1062 "Engineering linear F(ab')$_2$ fragments for efficient production in *Escherichia coli* and enhanced antiproliferative activity".

Zoller, M. et al., 1982, *Nucleic Acids Research*, 10(20):6487-6500 "Oligonucleotide-directed mutagenesis using M13-derived vectors: an efficient and general procedure for the production of point mutations in any fragment of DNA".

Albini et al., 1999, *Int. J. Biol. Markers*, 14:202-206.

Kisliouk et al., 2005, *Endocrinology*, 146:3950-3958.

Lin et al., 2002, *J. Biol. Chem.*, 277:19276-19280.

Risau, 1997, *Nature*, 386:671-674.

Stiffey-Wilusz et al., 2001, *Angiogenesis*, 4:3-9.

Yoshida et al., 2001, *Brain Tumor Pathol.*, 18-89-100.

Jiang et al., 2005, novel peptide isolated from a phage display peptide library with trastuzumab can mimic antigen epitope of HER-2. J. Biol. Chem. 280(6): 4656-4662.

Maldonado-Perez et al., 2007, "Potential roles of the prokineticins in reproduction." Trends Endo Met. 18(2): 66-71.

Pandya, et al., 2006, "Angiogenesis—a new target for future therapy." Vascular Pharm. 44:265-274.

Stancoviski et al., 1991, "Mechanistic aspects of the opposing effects of monoclonal antibodies to the ERBB2 receptor on tumor growth." Proc. Natl. Acad. Sci. 88(19): 8691-8695.

\* cited by examiner

FIGURE 1

TGAGGGCGCCATGAGGAGCCTGTGCTGCGCCCCACTCCTGCTCCTCTTGCTGCTGCCGCC
GCTGCTGCTCACGCCCCGCGCTGGGGACGCCGCCGTGATCACCGGGGCTTGTGACAAGGA
CTCCCAATGTGGTGGAGGCATGTGCTGTGCTGTCAGTATCTGGGTCAAGAGCATAAGGAT
TTGCACACCTATGGGCAAACTGGGAGACAGCTGCCATCCACTGACTCGTAAAAACAATTT
TGGAAATGGAAGGCAGGAAAGAAGAAAGAGGAAGAGAAGCAAAAGGAAAAAGGAGGTTCC
ATTTTTTGGGCGGAGGATGCATCACACTTGCCCATGTCTGCCAGGCTTGGCCTGTTTACG
GACTTCATTTAACCGATTTATTTGTTTAGCCCAAAAGTAATCGCTCTGGAGTAGAAACCA
AATGTGA

FIGURE 2

MRSLCCAPLLLLLLLLPPLLLTPRAGDAAVITGACDKDSQCGGGMCCAVSIWVKSIRICT
PMGKLGDSCHPLTRKNNFGNGRQERRKRKRSKRKKEVPFFGRRMHHTCPCLPGLACLRT
SFNRFICLAQK

Important features of the protein:

Signal sequence:
1-21

Transmembrane domain:
none cAMP- and cGMP-dependent protein kinase phosphorylation site:
    87-90

N-myristoylation site:
    41-46
    42-47
    43-48

Amidation site:
    99-102

FIGURE 3

GAGGGCGCCATGAGGAGCCTGTGCTGCGCCCCACTCCTGCTCCTCTTGCTGCTGCCGCCG
CTGCTGCTCACGCCCCGCGCTGGGGACGCCGCCGTGATCACCGGGGCTTGTGACAAGGAC
TCCCAATGTGGTGGAGGCATGTGCTGTGCTGTCAGTATCTGGGTCAAGAGCATAAGGATT
TGCACACCTATGGGCAAACTGGGAGACAGCTGCCATCCACTGACTCGTAAAGTTCCATTT
TTTGGGCGGAGGATGCATCACACTTGCCCATGTCTGCCAGGCTTGGCCTGTTTACGGACT
TCATTTAACCGATTTATTTGTTTAGCCCAAAAGTAATCGCTCTGGAGTAGAAACCAAATG
TGA

FIGURE 4

MRSLCCAPLLLLLLLLPPLLLTPRAGDAAVITGACDKDSQCGGGMCCAVSIWVKSIRICT
PMGKLGDSCHPLTRKVPFFGRRMHHTCPCLPGLACLRTSFNRFICLAQK

Important features of the protein:

Signal sequence:
1-21

Transmembrane domain:
none

N-myristoylation site:
    41-46
    42-47
    43-48

Amidation site:
    78-81

FIGURE 5

CGGACGCGTGGGCGTCCCCTAACCGCCACCGCGTCCCCGGGACGCC<u>ATG</u>GGGGACCCGCG
CTGTGCCCCGCTACTGCTACTTCTGCTGCTACCGCTGCTGTTCACACCGCCCGCCGGGGA
TGCCGCGGTCATCACCGGGGCTTGCGACAAGGACTCTCAGTGCGGAGGAGGCATGTGCTG
TGCTGTCAGTATCTGGGTTAAGAGCATAAGGATCTGCACACCTATGGGCCAAGTGGGCGA
CAGCTGCCACCCCTGACTCGGAAAGTTCCATTTTGGGGGCGGAGGATGCACCACACCTG
CCCCTGCCTGCCAGGCTTGGCGTGTTTAAGGACTTCTTTCAACCGGTTTATTTGCTTGGC
CCGGAAATGATCACTCTGAAG<u>TAG</u>GAACTTGAAATGCGACCCTCCGCTGCACAATGTCCG
TCGAGTCTCACTTGTAATTGTGGCAAACAAAGAATACTCCAGAAAGAAATGTTCTCCCCC
TTCCTTGACTTTCCAAGTAACGTTTCTATCTTTGATTTTTGAAGTGGCTTTTTTTTTTT
TTTTTTTCCTTTCCTTGAAGGAAAGTTTTGATTTTGGAGAGATTTATAGAGGACTTTC
TGACATGGCTTCTCATTTCCCTGTTTATGTTTTGCCTTGACATTTTTGAATGCCAATAAC
AACTGTTTTCACAAATAGGAGAATAAGAGGGAACAATCTGTTGCAGAAACTTCCTTTTGC
CCTTTGCCCCACTCGCCCCGCCCCGCCCCGCCCTGCCCATGCGCAGACAGACACA
CCCTTACTCTTCAAAGACTCTGATGATCCTCACCTTACTGTAGCATTGTGGGTTTCTACA
CTTCCCCGCCTTGCTGGTGGACCCACTGAGGAGGCTCAGAGAGCTAGCACTGTACAGGTT
TGAACCAGATCCCCCAAGCAGCTCATTTGGGGCAGACGTTGGGAGCGCTCCAGGAACTTT
CCTGCACCCATCTGGCCCACTGGCTTTCAGTTCTGCTGTTTAACTGGTGGGAGGACAAAA
TTAACGGGACCCTGAAGGAACCTGGCCCGTTTATCTAGATTTGTTTAAGTAAAAGACATT
TTCTCCTTGTTGTGGAATATTACATGTCTTTTTCTTTTTATCTGAAGCTTTTTTTTTT
TTCTTTAAGTCTTCTTGTTGGAGACATTTTAAAGAACGCCACTCGAGGAAGCATTGATTT
TCATYTGGCATGACAGGAGTCATCATTTTAAAAAATCGGTGTTAAGTTATAATTTAAACT
TTATTTGTAACCCAAAGGTYTAATGTAAATGGATTTCCTGATATCCTGCCATTTGTACTG
GTATCAATATTTYTATGT

FIGURE 6

MGDPRCAPLLLLLLLLPLLFTPPAGDAAVITGACDKDSQCGGGMCCAVSIWVKSIRICTP
MGQVGDSCHPLTRKVPFWGRRMHHTCPCLPGLACLRTSFNRFICLARK

Important features of the protein:

Signal sequence:
1-20

Transmembrane domain:
none

N-myristoylation site:
    40-45
    41-46
    42-47

Amidation site:
    77-80

Fig. 7

Human and mouse Bv8 are 96% identical

MRSLCCAPLLLLLLLPPLLLTPRAGDAAVITGACDKDSQCGGGMCCAVSI 50 human

MGDPRCAPLLLLLLLPPLLFTPRAGDAAVITGACDKDSQCGGGMCCAVSI 50 mouse

WVKSRICTPMGKLGDSCHPLTRKNNFGNGRQERRRKRSKRKKEVPFF-G

WVKSRICTPMGQVGDSCHPLTRKSHVANGRQERRRAKRRKRKKEVVPFWG

RRMHHTCPCLPGLACLRTSFNRFICLAQK

RRMHHTCPCLPGLACLRTSFNRFICLARK potential heparin-binding domain boxed

Note: this domain is not present in an alternative transcript

Fig. 8

Bv8 versus EG-VEGF

```
MRSLCCAPILILILILPPLILTPRAGDAAVITGACDKDSQCGGGMCCAVSI  50 Bv8
                 AVITGACERDVQCGAGTCCAISL  50 EG-VEGF

W VKSTRICTPMGKLGDSCHPLTRKNNFGNGRQERRRKRKRSKRKKEVPFFG
W LRGLRMCTPLGREGEECHPGSHK                       VPFFR

RRM HHTCPCLPGLACIRTSFNRFICLAQK
KRK HHTCPCLPNLLCSRFPDGRYRCSMDLKNINF
```

60% identity

Note: EG-VEGF does not contain a contiguous HB domain

Expression of human Bv8 detectable in the testis 1 pancreas
2 adrenal medulla
3 thyroid
4 adrenal cortex
5 testis
6 thymus
7 small intestine
8 stomach

Fig. 10
Expression of Bv8 in mouse and rat
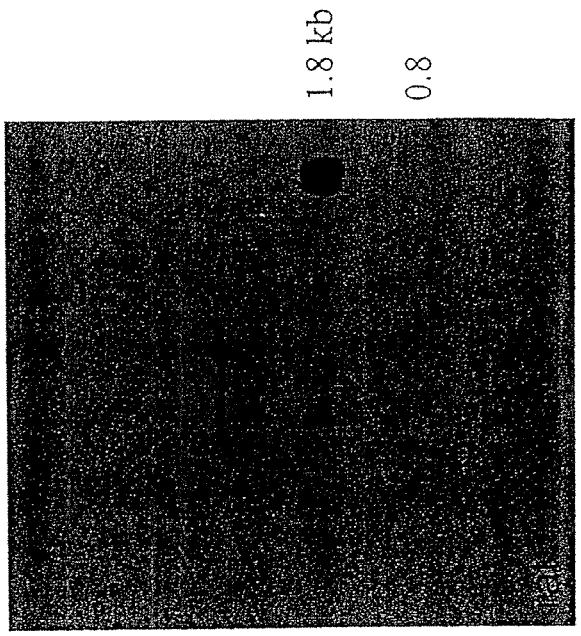
B.
5 liver
6 skeletal muscle
7 kidney
8 testis
1 heart
2 brain
3 spleen
4 lung
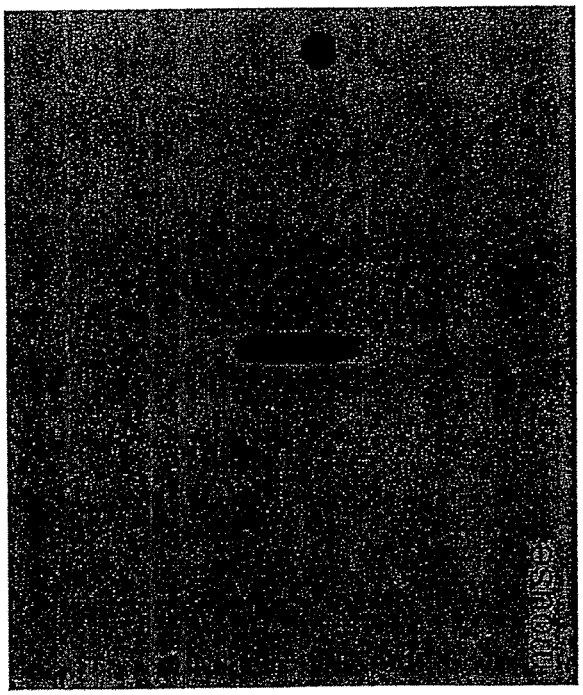
a - day 7
b - day 11
c - day 15
d - day 17
A.

SEQUENCE LISTING

<160> NUMBER OF SEQ ID NOS: 11

<210> SEQ ID NO 1
<211> LENGTH: 427
<212> TYPE: DNA
<213> ORGANISM: Homo sapiens
<220> FEATURE:
<223> OTHER INFORMATION: Nucleotide sequnece of a cDNA encoding a human Bv8 homologue

<400> SEQUENCE: 1

```
tgagggcgcc atgaggagcc tgtgctgcgc cccactcctg ctcctcttgc tgctgccgcc      60
gctgctgctc acgccccgcg ctggggacgc cgccgtgatc accggggctt gtgacaagga     120
ctcccaatgt ggtggaggca tgtgctgtgc tgtcagtatc tgggtcaaga gcataaggat     180
ttgcacacct atgggcaaac tgggagacag ctgccatcca ctgactcgta aaacaatttt     240
tggaaatgga aggcaggaaa gaagaaagag gaagagaagc aaaaggaaaa aggaggttcc     300
attttttggg cggaggatgc atcacacttg cccatgtctg ccaggcttgg cctgtttacg     360
gacttcattt aaccgattta tttgtttagc ccaaaagtaa tcgctctgga gtagaaacca     420
aatgtga                                                               427
```

<210> SEQ ID NO 2
<211> LENGTH: 129
<212> TYPE: PRT
<213> ORGANISM: Homo sapiens
<220> FEATURE:
<223> OTHER INFORMATION: Amino acid sequnece of a cDNA encoding a human Bv8 homologue

<400> SEQUENCE: 2

Met Arg Ser Leu Cys Cys Ala Pro Leu Leu Leu Leu Leu Leu Leu Pro
 1               5                  10                  15

Pro Leu Leu Leu Thr Pro Arg Ala Gly Asp Ala Ala Val Ile Thr Gly
                20                  25                  30

Ala Cys Asp Lys Asp Ser Gln Cys Gly Gly Gly Met Cys Cys Ala Val
            35                  40                  45

Ser Ile Trp Val Lys Ser Ile Arg Ile Cys Thr Pro Met Gly Lys Leu
        50                  55                  60

Gly Asp Ser Cys His Pro Leu Thr Arg Lys Asn Asn Phe Gly Asn Gly
65                  70                  75                  80

Arg Gln Glu Arg Arg Lys Arg Lys Arg Ser Lys Arg Lys Lys Glu Val
                85                  90                  95

Pro Phe Phe Gly Arg Arg Met His His Thr Cys Pro Cys Leu Pro Gly
            100                 105                 110

Leu Ala Cys Leu Arg Thr Ser Phe Asn Arg Phe Ile Cys Leu Ala Gln
        115                 120                 125

Lys

<210> SEQ ID NO 3
<211> LENGTH: 363
<212> TYPE: DNA
<213> ORGANISM: Homo sapiens
<220> FEATURE:
<223> OTHER INFORMATION: Nucleotide sequnece of a cDNA encoding an alternatively spliced version of the human Bv8 homologue

<400> SEQUENCE: 3

| | | |
|---|---|---|
| gagggcgcca tgaggagcct gtgctgcgcc ccactcctgc tcctcttgct gctgccgccg | 60 |
| ctgctgctca cgccccgcgc tggggacgcc gccgtgatca ccggggcttg tgacaaggac | 120 |
| tcccaatgtg gtggaggcat gtgctgtgct gtcagtatct gggtcaagag cataaggatt | 180 |
| tgcacaccta tgggcaaact gggagacagc tgccatccac tgactcgtaa agttccattt | 240 |
| tttgggcgga ggatgcatca cacttgccca tgtctgccag gcttggcctg tttacggact | 300 |
| tcatttaacc gatttatttg tttagcccaa aagtaatcgc tctggagtag aaaccaaatg | 360 |
| tga | 363 |

<210> SEQ ID NO 4
<211> LENGTH: 108
<212> TYPE: PRT
<213> ORGANISM: Homo sapiens
<220> FEATURE:
<223> OTHER INFORMATION: Amino acid sequnece of a cDNA encoding an alternatively spliced version of the human Bv8 homologue

<400> SEQUENCE: 4

```
Met Arg Ser Leu Cys Cys Ala Pro Leu Leu Leu Leu Leu Leu Pro
 1               5                  10                  15
Pro Leu Leu Leu Thr Pro Arg Ala Gly Asp Ala Ala Val Ile Thr Gly
            20                  25                  30
Ala Cys Asp Lys Asp Ser Gln Cys Gly Gly Gly Met Cys Cys Ala Val
        35                  40                  45
Ser Ile Trp Val Lys Ser Ile Arg Ile Cys Thr Pro Met Gly Lys Leu
    50                  55                  60
Gly Asp Ser Cys His Pro Leu Thr Arg Lys Val Pro Phe Phe Gly Arg
65                  70                  75                  80
Arg Met His His Thr Cys Pro Cys Leu Pro Gly Leu Ala Cys Leu Arg
                85                  90                  95
Thr Ser Phe Asn Arg Phe Ile Cys Leu Ala Gln Lys
            100                 105
```

<210> SEQ ID NO 5
<211> LENGTH: 1338
<212> TYPE: DNA
<213> ORGANISM: Mus musculus
<220> FEATURE:
<223> OTHER INFORMATION: Nucleotide sequence of mouse Bv8 homologue

<400> SEQUENCE: 5

| | | |
|---|---|---|
| cggacgcgtg gcgtcccct aaccgccacc gcgtccccgg acgccatggg ggacccgcg | 60 |
| ctgtgccccg ctactgctac ttctgctgct accgctgctg ttcacaccgc cgccggggga | 120 |
| tgccgcggtc atcaccgggg cttgcgacaa ggactctcag tgcggaggag gcatgtgctg | 180 |
| tgctgtcagt atctgggtta agagcataag gatctgcaca cctatgggcc aagtgggcga | 240 |
| cagctgccac cccctgactc ggaaagttcc attttggggg cggaggatgc accacacctg | 300 |
| cccctgcctg ccaggcttgg cgtgtttaag gacttctttc aaccggttta tttgcttggc | 360 |
| ccggaaatga tcactctgaa gtaggaactt gaaatgcgac cctccgctgc acaatgtccg | 420 |
| tcgagtctca cttgtaattg tggcaaacaa agaatactcc agaaagaaat gttctcccc | 480 |
| ttccttgact ttccaagtaa cgtttctatc tttgattttt gaagtggctt ttttttttt | 540 |

```
tttttttttcc tttccttgaa ggaaagtttt gattttttgga gagatttata gaggactttc      600
tgacatggct tctcatttcc ctgtttatgt tttgccttga cattttttgaa tgccaataac      660 aactgttttc acaaatagga gaataagagg gaacaatctg ttgcagaaac ttccttttgc      720
cctttgcccc actcgccccg ccccgccccg ccccgccctg cccatgcgca gacagacaca      780
cccttactct tcaaagactc tgatgatcct caccttactg tagcattgtg ggtttctaca      840
cttccccgcc ttgctggtgg acccactgag gaggctcaga gagctagcac tgtacaggtt      900
tgaaccagat cccccaagca gctcatttgg ggcagacgtt gggagcgctc caggaacttt      960
cctgcaccca tctggcccac tggctttcag ttctgctgtt taactggtgg gaggacaaaa     1020
ttaacgggac cctgaaggaa cctggcccgt ttatctagat ttgtttaagt aaaagacatt     1080
ttctccttgt tgtggaatat tacatgtctt tttctttttt atctgaagct ttttttttt       1140 ttctttaagt cttcttgttg gagacatttt aaagaacgcc actcgaggaa gcattgattt     1200
tcatytggca tgacaggagt catcatttta aaaaatcggt gttaagttat aatttaaact     1260
ttatttgtaa cccaaaggty taatgtaaat ggatttcctg atatcctgcc atttgtactg     1320
gtatcaatat ttytatgt                                                   1338

<210> SEQ ID NO 6
<211> LENGTH: 107
<212> TYPE: PRT
<213> ORGANISM: Mus musculus
<220> FEATURE:
<223> OTHER INFORMATION: Amino acid sequence of mouse Bv8 homologue

<400> SEQUENCE: 6

Met Gly Asp Pro Arg Cys Ala Pro Leu Leu Leu Leu Leu Leu Leu Pro
  1               5                  10                  15

Leu Leu Phe Thr Pro Pro Ala Gly Asp Ala Ala Val Ile Thr Gly Ala
             20                  25                  30

Cys Asp Lys Asp Ser Gln Cys Gly Gly Gly Met Cys Cys Ala Val Ser
         35                  40                  45

Ile Trp Val Lys Ser Ile Arg Ile Cys Thr Pro Met Gly Gln Val Gly
     50                  55                  60

Asp Ser Cys His Pro Leu Thr Arg Lys Val Pro Phe Trp Gly Arg Arg
 65                  70                  75                  80

Met His His Thr Cys Pro Cys Leu Pro Gly Leu Ala Cys Leu Arg Thr
                 85                  90                  95

Ser Phe Asn Arg Phe Ile Cys Leu Ala Arg Lys
            100                 105

<210> SEQ ID NO 7
<211> LENGTH: 86
<212> TYPE: PRT
<213> ORGANISM: Homo sapiens
<220> FEATURE:
<223> OTHER INFORMATION: EG-VEGF sequence

<400> SEQUENCE: 7

Ala Val Ile Thr Gly Ala Cys Glu Arg Asp Val Gln Cys Gly Ala Gly
  1               5                  10                  15

Thr Cys Cys Ala Ile Ser Leu Trp Leu Arg Gly Leu Arg Met Cys Thr
             20                  25                  30

Pro Leu Gly Arg Glu Gly Glu Glu Cys His Pro Gly Ser His Lys Val
         35                  40                  45
```

```
Pro Phe Phe Arg Lys Arg Lys His His Thr Cys Pro Cys Leu Pro Asn
    50                  55                  60

Leu Leu Cys Ser Arg Phe Pro Asp Gly Arg Tyr Arg Cys Ser Met Asp
 65                  70                  75                  80

Leu Lys Asn Ile Asn Phe
                85

<210> SEQ ID NO 8
<211> LENGTH: 102
<212> TYPE: PRT
<213> ORGANISM: Mus musculus
<220> FEATURE:
<223> OTHER INFORMATION: Amino acid sequence of mouse Bv8 homologue
      with heparin-binding domain

<400> SEQUENCE: 8

Ala Val Ile Thr Gly Ala Cys Asp Lys Asp Ser Gln Cys Gly Gly Gly
  1               5                  10                  15

Met Cys Cys Ala Val Ser Ile Trp Val Lys Ser Ile Arg Ile Cys Thr
                 20                  25                  30

Pro Met Gly Gln Val Gly Asp Ser Cys His Pro Leu Thr Arg Lys Ser
             35                  40                  45

His Val Ala Asn Gly Arg Gln Glu Arg Arg Ala Lys Arg Lys
 50                  55                  60

Arg Lys Lys Glu Val Pro Phe Trp Gly Arg Arg Met His His Thr Cys
 65                  70                  75                  80

Pro Cys Leu Pro Gly Leu Ala Cys Leu Arg Thr Ser Phe Asn Arg Phe
                 85                  90                  95

Ile Cys Leu Ala Arg Lys
            100

<210> SEQ ID NO 9
<211> LENGTH: 6
<212> TYPE: DNA
<213> ORGANISM: Artificial Sequence
<220> FEATURE:
<223> OTHER INFORMATION: Nucelotide sequence found 70-80 bases upstream
      from start of eukaryotic transcription.
<220> FEATURE:
<221> NAME/KEY: variation
<222> LOCATION: (2)...(2)
<223> OTHER INFORMATION: n = any nucleotide

<400> SEQUENCE: 9 cncaat                                                            6

<210> SEQ ID NO 10
<211> LENGTH: 6
<212> TYPE: DNA
<213> ORGANISM: Artificial Sequence
<220> FEATURE:
<223> OTHER INFORMATION: Sequence signalling addition of the poly-A
      tail to 3-prime end of eukaryotic coding sequence

<400> SEQUENCE: 10 aataaa                                                            6

<210> SEQ ID NO 11
<211> LENGTH: 10
<212> TYPE: PRT
<213> ORGANISM: Artificial Sequence
<220> FEATURE:
<223> OTHER INFORMATION: Amino acid sequence of the IgG1 hinge region of
      the Bv8 part of the molecule
```

```
<400> SEQUENCE: 11

Asp Lys Thr His Thr Cys Pro Pro Cys Pro
1               5                   10
```

BV8 NUCLEIC ACIDS AND POLYPEPTIDES WITH MITOGENIC ACTIVITY

REFERENCE TO RELATED APPLICATION

This application is a continuation of U.S. application Ser. No. 11/384,222, filed Mar. 17, 2006, which is a continuation of U.S. application Ser. No. 10/231,411, filed Aug. 27, 2002, now U.S. Pat. No. 7,060,278, which claims priority under 35 U.S.C. §119(e) to U.S. Provisional Application No. 60/316,184, filed Aug. 29, 2001, all of which are hereby incorporated herein by reference.

FIELD OF THE INVENTION

The present invention relates generally to methods, compositions and assays using Bv8, a protein with mitogenic activities.

BACKGROUND OF THE INVENTION

Endothelial Cells

The local microenvironment profoundly affects the phenotype and growth properties of vascular endothelial cells in a tissue- or organ-specific manner, but the nature of the local instructive signals is largely unknown. There is compelling evidence that the vascular endothelial growth factor (VEGF) and angiopoietin families of endothelial cell specific growth factors are essential for embryonic development and for angiogenesis in a variety of physiological and pathological circumstances (Ferrara and Alitalo, *Nature Medicine*, 5:1359-1364 (1999); Carmeliet, *Nature Medicine*, 6:389-395 (2000)). There is also strong evidence for a local, tissue-specific, regulation of endothelial cell phenotype and growth (Aird et al., *J. Cell Biol.*, 138:1117-1124 (1997); Stewart and Wiley, *Dev. Biol.*, 84:183-192 (1981)). The morphological and functional characteristics of endothelial cells vary extensively among different organs (Simionescu and Simionescu, *Cell and Tissue Biology*, Urban and Schwarzemberg, Baltimore, (1988) pp. 355-398). Furthermore, the site of application determines the properties of new vessels to an even greater extent than the type of angiogenic factor tested (Dellian et al., *Am. J. Pathology*, 149:59-71 (1996); Roberts et al., *Am. J. Pathology*, 153:1239-1248 (1998)). The molecular basis for this influence of the local microenvironment on the properties of the vasculature is unknown, but it is believed that the specialized stroma plays a major role (Dellian, supra). Conceivably, an integrated network of stimuli, which may include tissue-specific secreted proteins, in addition to cellular and extracellular matrix components, functions to determine the structure and function as well as modulate growth of the resident endothelium.

Thus there is a current need to identify and characterize factors that influence the growth and/or differentiation of endothelial cells. In addition to increasing our knowledge of the development of the vasculature, such compounds could be useful in the diagnosis and treatment of conditions associated with vascular tissue.

Hormone Secreting Cells

While there has been progress in the advancement of science and medical therapies, there is still a need for new treatments for the medical ailments of society. One approach to finding new treatments has been to study how the organism operates. In particular, of interest is how signaling cells control the behavior of the organism. For example, endocrine cells secrete signaling molecules called hormones wherein malfunctioning of secretion of these hormones can lead to a variety of disorders.

Cells specialized for secretion of hormones include the cells of gonads, secreting testosterone (Leydig cell of testis), estrogen (theca interna cell of ovarian follicle) and progesterone (corpus luteum cell of ruptured ovarian follicle). While there are a variety of treatments in the medical field which utilize exogenous administration of testosterone, estrogen and progesterone, there remains a need to regulate the cells which produce these hormones.

Other cells specialized for hormone secretion include the cells of the adrenal gland and the cells of the digestive system. For example, cells of the adrenal gland secrete epinephrine, norepinephrine and steroid hormones such as mineralocorticoids and glucocorticoids. Of particular interest is cortisol which is produced in the cortex of the adrenal gland and which influences the metabolism of many cell types. Cells of the digestive system include those of the pancreas which secrete insulin. Insulin is secreted by the islets of Langerhans and is essential for the metabolism of carbohydrates. Insulin is used in the treatment and control of diabetes mellitus, however, there is still a need for efficient treatments for disorders such as diabetes. Other hormones of interest of the gut and respiratory tract include serotonin, endorphin, somatostatin, gastrin, secretin, cholecystokinin, glucagon and bombesin.

There are numerous diseases and disorders associated with hormone secreting cells, in particular steroidogenic endothelial cells within endocrine glands. It would, therefore, be desirable to identify growth factors specifically affecting such endothelial cells. Such endothelial cell specific growth factors would be valuable tools for diagnosing and treating disorders associated with such cell types, and for identifying further drug candidates useful in diagnosis and treatment of such diseases.

Bv8

Bv8 is a small protein that was originally isolated from the skin secretions of the frog *Bombina variegata* (Mollay et al. *Eur. J. Pharmacol.* 374:189-196 (1999)). Bv8 shows greater than 40% identity with MIT-1, a small protein from black mamba venom that has been shown to be highly potent in inducing intestinal contraction (Schweitz et al. *FEBS Lett.* 461:183-188 (1999)). Several mammalian homologues of Bv8 have been cloned from mouse and human and have been shown to have identical amino-terminal sequences (Wechselberger et al. *FEBS Lett.* 462:177-181 (1999)). Like MIT-1, human Bv8 has been shown to potently contract gastrointestinal smooth muscle, with an EC.sub.50 in the subnanomolar range (Li et al. *Mol. Pharm.* 59:692-698 (2001)). Two forms of Bv8 have been identified in humans, the longer form reflecting the presence of an alternatively spliced exon. The longer form of human Bv8 is approximately 78% homologous and 58% identical to VRPA, described in U.S. patent application Ser. No. 09/886,242, which is hereby incorporated by reference.

SUMMARY OF THE INVENTION

The present invention is based on the identification of novel activities of Bv8. In particular, Bv8 has been found to induce proliferation in endothelial cells, to promote survival of endothelial cells and to promote angiogenesis. As described in detail herein, Bv8 nucleic acids and polypeptides can be used in a number of assays and in diagnosis and treatment of conditions associated with endothelial cells.

In one aspect, the present invention provides a method of inducing cell proliferation. In one embodiment the method comprises contacting cells with Bv8 in an amount effective to induce proliferation of the cells. The method may further comprise contacting the cells with VEGF. In another embodiment the method comprises introducing nucleic acid encoding Bv8 into cells in an amount effective to induce cell proliferation. This method may further comprise introducing a nucleic acid encoding VEGF to the cells.

In one embodiment the Bv8 is a native sequence Bv8 polypeptide. Preferably, the native sequence Bv8 polypeptide is a native human Bv8 polypeptide. The native human Bv8 polypeptide may comprise the amino acid sequence of SEQ ID NO: 2 or the amino acid sequence of SEQ ID NO: 4. In another embodiment the native sequence Bv8 comprises the amino acid sequence of SEQ ID NO: 6. In another embodiment the Bv8 is capable of heparin binding. In yet another embodiment the Bv8 is a Bv8 immunoadhesin. In a further embodiment the Bv8 is chimeric Bv8.

In one embodiment the cells are endothelial cells, more preferably steroidogenic endothelial cells such as the cells of a steroidogenic gland.

In a further aspect the invention provides a method of enhancing cell survival. In one embodiment this method comprises contacting the cells with Bv8 in an amount effective to enhance survival. The method may further comprise contacting the cells with VEGF. In another embodiment this method comprises introducing nucleic acid encoding Bv8 into cells in an amount effective to enhance cell survival. This method may further comprise introducing a nucleic acid encoding VEGF to the cells.

In one embodiment the Bv8 is a native sequence Bv8 polypeptide. Preferably, the native sequence Bv8 polypeptide is a native human Bv8 polypeptide. The native human Bv8 polypeptide may comprise the amino acid sequence of SEQ ID NO: 2 or the amino acid sequence of SEQ ID NO: 4. In another embodiment the native sequence Bv8 comprises the amino acid sequence of SEQ ID NO: 6. In another embodiment the Bv8 is heparin binding.

The cells are preferably endothelial cells, more preferably steroidogenic endothelial cells such as the cells of a steroidogenic gland.

In a further aspect, the present invention provides a method of treating a mammal for a condition associated with hormone producing tissues. In one embodiment the method preferably comprises administering to the mammal a composition comprising Bv8 or an agonist or antagonist thereof in an amount effective to treat the condition. In another embodiment the method further comprises administering VEGF or an agonist or antagonist thereof to the mammal. The mammal is preferably human.

In one embodiment the Bv8 is heparin biding. In another embodiment the Bv8 is a native sequence Bv8 polypeptide. Preferably, the native sequence Bv8 polypeptide is a native human Bv8 polypeptide. The native human Bv8 polypeptide may comprise the amino acid sequence of SEQ ID NO: 2 or the amino acid sequence of SEQ ID NO: 4. In another embodiment the native sequence Bv8 comprises the amino acid sequence of SEQ ID NO: 6.

In yet a further aspect the invention provides a method of inhibiting endothelial cell proliferation. In one embodiment the method comprises contacting the endothelial cells with a Bv8 antagonist in an amount effective to inhibit cell proliferation.

In a still further aspect the present invention provides a method of treating cancer in cells responsive to Bv8 in a mammal, preferably a human. The method preferably comprises administering a Bv8 antagonist in an amount effective to treat the cancer. In one embodiment the cancer is hormone-dependent cancer. In another embodiment the cancer is testicular cancer.

In another aspect the present invention provides a method of treating cancer of the reproductive organs in a mammal, preferably a human. In one embodiment the method comprises administering a Bv8 antagonist to the mammal in an amount effective to treat the cancer. The cancer is preferably testicular cancer.

In another aspect the present invention provides a method of inducing angiogenesis. In one embodiment, this method comprises contacting cells with Bv8 in an amount effective to induce angiogenesis. In another embodiment, this method comprises introducing nucleic acid encoding Bv8 into cells in an amount effective to induce angiogenesis.

In a further aspect, the present invention provides a method of treating a mammal for a condition associated with excessive, unwanted or uncontrolled angiogenesis. In one embodiment the method preferably comprises administering to the mammal Bv8 or an agonist or antagonist thereof in an amount effective to treat the disease. The mammal is preferably human.

In an even further aspect the invention provides a method of regulating fertility in a mammal. In one embodiment the mammal is human. The method preferably comprises administering a Bv8 antagonist to the mammal in an amount effective to regulate fertility.

In a still further aspect the invention provides an article of manufacture comprising a container, Bv8 and instructions for using the Bv8. In one embodiment the instructions are for using the Bv8 to treat a condition that is associated with hormone producing endothelial tissue, preferably testicular tissue.

In another aspect the invention provides a method of treating a steroid hormone-dependent disorder in a mammal. In one embodiment the method comprises administering Bv8 or an agonist or antagonist thereof to the mammal in an amount effective to treat the steroid hormone-dependent disorder. Preferably the mammal is a human. The steroid-hormone dependent disorder is preferably selected from the group consisting of lipoid congenital adrenal hyperplasia, infertility, sexual maturation, androgen-dependent tumors, precocious puberty, McCune-Albright syndrome, adrenal-hypoplasia congenita, and hypogonadotropic hypogonadism.

In another aspect the invention provides an article of manufacture comprising a container, a Bv8 antagonist and instructions for using the Bv8 antagonist. In one embodiment the instructions are for using the Bv8 antagonist to treat cancer, preferably testicular cancer. In another embodiment the instructions are for using the Bv8 antagonist to regulate fertility.

Another aspect of the invention provides a method for identifying a Bv8 antagonist by contacting a candidate compound with Bv8, determining the effect of the compound on a Bv8 biological activity and identifying an antagonist where a Bv8 biological activity is inhibited. In one embodiment a Bv8 antagonist is identified by its inhibition of the ability of Bv8 to stimulate endothelial cell proliferation. In another embodiment a Bv8 antagonist is identified by its inhibition of the ability of Bv8 to promote endothelial cell survival.

BRIEF DESCRIPTION OF THE DRAWINGS

FIG. 1 shows the nucleotide sequence (SEQ ID NO: 1) of a cDNA encoding a human Bv8 homologue. Also presented in bold font and underlined are the positions of the respective start and stop codons.

FIG. 2 shows the amino acid sequence (SEQ ID NO: 2) of a human Bv8 homologue polypeptide as derived from the coding sequence of SEQ ID NO: 1. A putative signal sequence is comprised of amino acids 1 through 21.

FIG. 3 shows the nucleotide sequence (SEQ ID NO: 3) of a cDNA encoding an alternatively spliced version of the human Bv8 homologue. Also presented in bold font and underlined are the positions of the respective start and stop codons.

FIG. 4 shows the amino acid sequence (SEQ ID NO: 4) of a human Bv8 homologue polypeptide as derived from the coding sequence of SEQ ID NO: 3.

FIG. 5 shows the nucleotide sequence (SEQ ID NO: 5) of a mouse Bv8 homologue. Also presented in bold font and underlined are the positions of the respective start and stop codons.

FIG. 6 shows the amino acid sequence (SEQ ID NO: 6) of a mouse Bv8 homologue polypeptide as derived from the coding sequence of SEQ ID NO: 5.

FIG. 7 shows an alignment of the mouse (SEQ ID NO:8) and human (SEQ ID NO:2) Bv8 homologues. A potential heparin-binding domain is boxed. As indicated, this domain is not present in an alternatively spliced transcript. The mouse and human Bv8 homologues are approximately 96% identical.

FIG. 8 shows an alignment of the amino acid sequences of human Bv8 (SEQ ID NO:2) and EG-VEGF (SEQ ID NO:7). Human Bv8 is approximately 60% identical to human EG-VEGF.

FIGS. 10A and 10B show northern blot analysis of expression of Bv8 in the mouse and rat. In mouse, Bv8 expression can be seen in the heart and in the testis (FIG. 10A). In rat, Bv8 expression is only visible in the testis (FIG. 10B). In addition, a smaller band of 0.8 kb is also visible in rat testis.

FIG. 11A shows that administration of Bv8 at concentrations of 1, 10 and 50 nM increases proliferation of bovine adrenal cortical capillary endothelial (ACE) cells compared to untreated controls ("C"). Similarly, FIG. 11B indicates that Bv8 at all three concentrations increases proliferation of bovine brain capillary cells. In both cases, proliferation induced by Bv8 is less than that induced by VEGF ("V").

DETAILED DESCRIPTION OF THE PREFERRED EMBODIMENTS

I. Definitions

Figure 9:
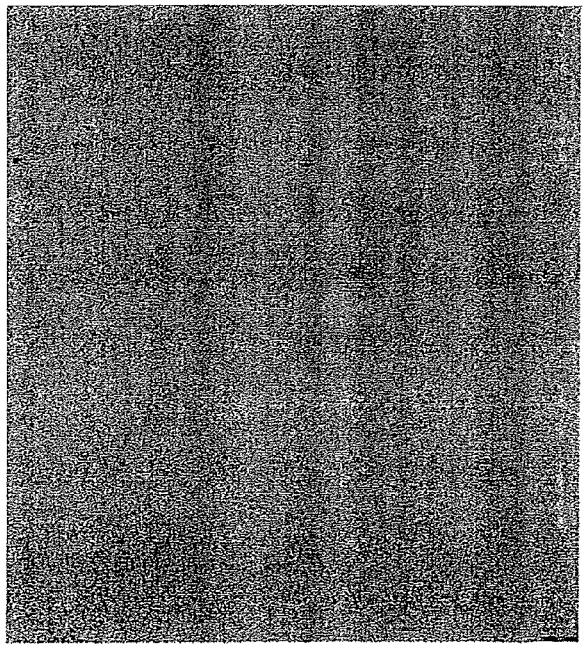
FIG. 9 Northern blot analyses of human RNA samples revealed a single transcript of approximately 1.8 kb. Expression was visible in testis. Contents of the lanes are indicated above the blots, and the size (kb) is indicated at the right.

Unless defined otherwise, technical and scientific terms used herein have the same meaning as commonly understood by one of ordinary skill in the art to which this invention belongs. See, e.g. Singleton et al., *Dictionary of Microbiology and Molecular Biology* 2nd ed., J. Wiley & Sons (New York, N.Y. 1994); Sambrook et al., *Molecular Cloning, A Laboratory Manual*, Cold Springs Harbor Press (Cold Springs Harbor, N.Y. 1989). For purposes of the present invention, the following terms are defined below.

As used herein, the terms "Bv8" and "Bv8 polypeptide," which are used interchangeably, refer to native sequence Bv8, Bv8 variants, and chimeric Bv8, each of which is defined herein. Optionally, the Bv8 is not associated with native glycosylation. "Native glycosylation" refers to the carbohydrate moieties that are covalently attached to Bv8 when it is produced in mammalian cells, particularly in the cells in which it is produced in nature. Accordingly, human Bv8 produced in a non-human cell is an example of Bv8 that may "not be associated with native glycosylation." Sometimes the Bv8 may not be glycosylated at all, as in the case where it is produced in prokaryotes, e.g. *E. coli*.

Bv8 nucleic acid is RNA or DNA that encodes a Bv8 polypeptide, as defined above, or which hybridizes to such DNA or RNA and remains stably bound to it under stringent hybridization conditions and is greater than about 10 nucleotides in length. Stringent conditions are those which (1) employ low ionic strength and high temperature for washing, for example, 0.15 M NaCl/0.015 M sodium citrate/0.1% NaDodSO$_4$ at 50° C., or (2) use during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.

Nucleic acid is operably linked when it is placed into a functional relationship with another nucleic acid sequence. Bv8 nucleic acid may be operably linked with another nucleic acid sequence in a vector such that it may be expressed in a particular host organism. This may be done by methods well known in the art. For example, DNA for a presequence or a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adapters or linkers are used in accord with conventional practice.

"Native sequence Bv8" comprises a polypeptide having the same amino acid sequence as Bv8 derived from nature, regardless of its mode of preparation. Thus, native sequence Bv8 can have the amino acid sequence of naturally occurring human Bv8, murine Bv8, or Bv8 from any other mammalian species. For example a full-length native sequence human Bv8 amino acid sequence is shown in FIG. 2 (SEQ ID NO: 2). A second full-length native sequence human Bv8 is shown in FIG. 4 (SEQ ID NO: 4). These two sequences are the result of the alternative splicing of an exon that encodes a canonical heparin binding domain. Thus the native sequence human Bv8 whose amino acid sequence is shown in FIG. 2 (SEQ ID NO: 2) comprises a heparin binding domain, while the native sequence Bv8 depicted in FIG. 4 (SEQ ID NO: 4) does not. A native sequence mouse Bv8 amino acid sequence is shown in FIG. 6 (SEQ ID NO: 6). Human and murine Bv8 sequences are also disclosed, for example, in Wechselberger et al. (FEBS Lett. 462:177-181 (1999)) and Li et al. (Mol. Pharm. 59:692-698 (2001)). Such native sequence Bv8 can be isolated from nature or can be produced by recombinant and/or synthetic means. The term "native sequence Bv8" specifically encompasses naturally occurring prepro, pro and mature forms and truncated forms of Bv8, naturally occurring variant forms (e.g. alternatively spliced forms, such as that shown in FIG. 4 (SEQ ID NO: 4)), and naturally occurring allelic variants. A preferred native sequence Bv8 is a full-length native sequence human Bv8 as shown in FIG. 2 (SEQ ID NO: 2).

"Bv8 variants" are biologically active Bv8 polypeptides having an amino acid sequence which differs from the sequence of a native sequence Bv8 polypeptide, such as those shown in FIGS. 2, 4 and 6 (SEQ ID NOs: 2, 4 and 6) for human and murine Bv8, by virtue of an insertion, deletion, modification and/or substitution of one or more amino acid residues within the native sequence. Bv8 variants generally have less than 100% sequence identity with a native sequence Bv8, such as the human Bv8 of FIG. 2 (SEQ ID NO: 2). Ordinarily, however, a biologically active Bv8 variant will have an amino acid sequence with at least about 70% amino acid sequence identity with the amino acid sequence of a naturally occurring Bv8 such as the human Bv8 of FIG. 2 (SEQ ID NO: 2), preferably at least about 75%, more preferably at least about 80%, even more preferably at least about 85%, even more preferably at least about 90%, with increasing preference of at least about 95% to at least about 99% amino acid sequence identity, in 1% increments. The Bv8 variants include peptide fragments of at least 5 amino acids that retain a biological activity of the corresponding native sequence Bv8 polypeptide. Bv8 variants also include Bv8 polypeptides wherein one or more amino acid residues are added at the N- or C-terminus of, or within, a native Bv8 sequence. Bv8 variants also include Bv8 polypeptides where a number of amino acid residues are deleted and optionally substituted by one or more amino acid residues. Bv8 variants also may be covalently modified, for example by substitution with a moiety other than a naturally occurring amino acid or by modifying an amino acid residue to produce a non-naturally occurring amino acid. Bv8 variants may comprise a heparin binding domain.

"Percent amino acid sequence identity" with respect to the Bv8 sequence is defined herein as the percentage of amino acid residues in the candidate sequence that are identical with the residues in the Bv8 sequence, after aligning the sequences and introducing gaps, if necessary, to achieve the maximum percent sequence identity, and not considering any conservative substitutions as part of the sequence identity. None of N-terminal, C-terminal, or internal extensions, deletions or insertions into the candidate Bv8 sequence shall be construed as affecting sequence identity or homology. Methods and computer programs for the alignment are well known in the art. One such computer program is "ALIGN-2," authored by Genentech, Inc., which has been filed with user documentation in the United States Copyright Office, Washington, D.C. 20559, where it is registered under U.S. Copyright Registration No. TXU510087.

A "chimeric Bv8" molecule is a polypeptide comprising full-length Bv8 or one or more domains thereof fused or bonded to heterologous polypeptide. The chimeric Bv8 molecule will generally share at least one biological property in common with naturally occurring Bv8. An example of a chimeric Bv8 molecule is one that is epitope tagged for purification purposes. Another chimeric Bv8 molecule is a Bv8 immunoadhesin.

The term "epitope-tagged" when used herein refers to a chimeric polypeptide comprising Bv8 fused to a "tag polypeptide". The tag polypeptide has enough residues to provide an epitope against which an antibody can be made, yet is short enough such that it does not interfere with biological activity of the Bv8. The tag polypeptide preferably is fairly unique so that the antibody against it does not substantially cross-react with other epitopes. Suitable tag polypeptides generally have at least six amino acid residues and usually between about 8-50 amino acid residues (preferably between about 9-30 residues). Preferred are poly-histidine sequences, which bind nickel, allowing isolation of the tagged protein by Ni-NTA chromatography as described (See, e.g., Lindsay et al. *Neuron* 17:571-574 (1996)).

"Isolated Bv8" means Bv8 that has been purified from a Bv8 source or has been prepared by recombinant or synthetic methods and purified. Purified Bv8 is substantially free of other polypeptides or peptides. "Substantially free" here means less than about 5%, preferably less than about 2%, more preferably less than about 1%, even more preferably less than about 0.5%, most preferably less than about 0.1% contamination with other source proteins.

"Essentially pure" protein means a composition comprising at least about 90% by weight of the protein, based on total weight of the composition, preferably at least about 95% by weight, more preferably at least about 90% by weight, even more preferably at least about 95% by weight. "Essentially homogeneous" protein means a composition comprising at least about 99% by weight of protein, based on total weight of the composition.

Bv8 "agonists" are molecules or compounds that have one or more of the biological properties of native sequence Bv8. These may include, but are not limited to, small organic molecules, peptides, and agonist anti-Bv8 antibodies.

The term "antagonist" is used in the broadest sense, and includes any molecule that partially or fully blocks, inhibits, or neutralizes a biological activity of a native Bv8 polypeptide. Suitable antagonist molecules specifically include antagonist antibodies or antibody fragments, fragments or amino acid sequence variants of native Bv8 polypeptides, peptides, small organic molecules, etc. Methods for identifying agonists or antagonists of a Bv8 polypeptide may comprise contacting a Bv8 polypeptide with a candidate agonist or antagonist molecule and measuring a detectable change in one or more biological activities normally associated with the Bv8 polypeptide.

"Active" or "activity" for the purposes herein refers to form(s) of Bv8 which retain a biological and/or an immunological activity of native or naturally-occurring Bv8, wherein "biological" activity refers to a biological function (either inhibitory or stimulatory) caused by a native or naturally-occurring Bv8 other than the ability to induce the production of an antibody against an antigenic epitope possessed by a native or naturally-occurring Bv8 and an "immunological" activity refers to the ability to induce the production of an antibody against an antigenic epitope possessed by a native or naturally-occurring Bv8.

Thus, "biologically active" when used in conjunction with "Bv8" or "isolated Bv8" or an agonist of Bv8, means a Bv8 polypeptide that exhibits or shares an effector function of native sequence Bv8. A principal effector function of Bv8 is its ability to stimulate the proliferation of endothelial cells.

Even more preferably, the biological activity is the ability to induce proliferation in capillary endothelial cells, preferably steroidogenic cells, within endocrine glands. A further effector function of Bv8 is its ability to induce angiogenesis.

"Biological property" when used in conjunction with "Bv8" or "isolated Bv8" or an "agonist" of Bv8, means having an effector or antigenic function or activity that is directly or indirectly caused or performed by native sequence Bv8 (whether in its native or denatured conformation). Effector functions include enhancement of proliferation of endothelial cells and/or induction of angiogenesis.

"Bv8 receptor" is a molecule to which Bv8 binds and which mediates the biological properties of Bv8.

The term "antibody" herein is used in the broadest sense and specifically covers human, non-human (e.g. murine) and humanized monoclonal antibodies (including full length monoclonal antibodies), polyclonal antibodies, multispecific antibodies (e.g., bispecific antibodies), and antibody fragments so long as they exhibit the desired biological activity.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3 and FR4, respectively), largely adopting a 9-sheet configuration, connected by three hypervariable regions, which form loops connecting, and in some cases forming part of, the S-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen binding. The hypervariable region comprises amino acid residues from a "complementarity determining region" or "CDR" (i.e. residues 24-34 (L1(50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (i.e. residues 26-32 (L1(, 50-52 (L2) and 91-96 (L3) in the light chain variable domain and 26-32 (H1), 53-55 (H2) and 96-101 (H3) in the heavy chain variable domain; Chothia and Lesk, *J. Mol. Biol.* 196:901-917 (1987)). "Framework" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment that contains a complete antigen-recognition and -binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (P) and lambda ($\Sigma$), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2.

The heavy-chain constant domains that correspond to the different classes of immunoglobulins are called $\alpha$, $\delta$, $\epsilon$, $\gamma$, and $\mu$, respectively. The subunit structures and three-dimensional configurations of different classes of immunoglobulins are well known.

"Antibody fragments" comprise a portion of a full-length antibody, generally the antigen binding or variable domain thereof. Examples of antibody fragments include Fab, Fab', F(ab')$_2$, and Fv fragments; diabodies; linear antibodies; single-chain antibody molecules; and multi-specific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Reichmann et al., *Nature* 332:323-329 (1988); and Presta, *Curr. Op. Struct. Biol.* 2:593-596 (1992).

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444-6448 (1993).

The expression "linear antibodies" when used throughout this application refers to the antibodies described in Zapata et al. Protein Eng. 8(10):1057-1062 (1995). Briefly, these antibodies comprise a pair of tandem Fd segments ($V_H$-$C_H$1-$V_{H-CH}$1) which form a pair of antigen binding regions. Linear antibodies can be bispecific or monospecific.

The term "epitope" is used to refer to binding sites for (monoclonal or polyclonal) antibodies on protein antigens.

By "agonist antibody" is meant an antibody that is a Bv8 agonist and thus possesses one or more of the biological properties of native sequence Bv8.

The term "Bv8 immunoadhesin" is used interchangeably with the term "Bv8-immunoglobulin chimera", and refers to a chimeric molecule that combines at least a portion of a Bv8 molecule (native or variant) with an immunoglobulin sequence. The immunoglobulin sequence preferably, but not necessarily, is an immunoglobulin constant domain. Immunoadhesins can possess many of the valuable chemical and biological properties of human antibodies. Since immunoadhesins can be constructed from a human protein sequence with a desired specificity linked to an appropriate human immunoglobulin hinge and constant domain (Fe) sequence, the binding specificity of interest can be achieved using entirely human components. Such immunoadhesins are minimally immunogenic to the patient, and are safe for chronic or repeated use.

Examples of homomultimeric immunoadhesins which have been described for therapeutic use include the CD4-IgG immunoadhesin for blocking the binding of HIV to cell-surface CD4. Data obtained from Phase I clinical trials, in which CD4-IgG was administered to pregnant women just before delivery, suggests that this immunoadhesin may be useful in the prevention of maternal-fetal transfer of HIV (Ashkenazi et al., Intern. Rev. Immunol. 10:219-227 (1993)). An immunoadhesin which binds tumor necrosis factor (TNF) has also been developed. TNF is a proinflammatory cytokine which has been shown to be a major mediator of septic shock. Based on a mouse model of septic shock, a TNF receptor immunoadhesin has shown promise as a candidate for clinical use in treating septic shock (Ashkenazi, A. et al. (1991) PNAS USA 88:10535-10539). ENBREL® (etanercept), an immunoadhesin comprising a TNF receptor sequence fused to an IgG Fc region, was approved by the U.S. Food and Drug Administration (FDA), on Nov. 2, 1998, for the treatment of rheumatoid arthritis. The new expanded use of ENBREL® in the treatment of rheumatoid arthritis was approved by FDA on Jun. 6, 2000. For recent information on TNF blockers, including ENBREL®, see Lovell et al., *N Engl. J. Med.* 342: 763-169 (2000), and accompanying editorial on p 810-811; and Weinblatt et al., *N. Engl. J. Med.* 340: 253-259 (1999); reviewed in Maini and Taylor, *Annu. Rev. Med.* 51: 207-229 (2000).

If the two arms of the immunoadhesin structure have different specificities, the immunoadhesin is called a "bispecific immunoadhesin" by analogy to bispecific antibodies. Dietsch et al., *J. Immunol. Methods* 162:123 (1993) describe such a bispecific immunoadhesin combining the extracellular domains of the adhesion molecules, E-selectin and P-selectin, each of which selectins is expressed in a different cell type in nature. Binding studies indicated that the bispecific immunoglobulin fusion protein so formed had an enhanced ability to bind to a myeloid cell line compared to the monospecific immunoadhesins from which it was derived.

The term "heteroadhesin" is used interchangeably with the expression "chimeric heteromultimer adhesin" and refers to a complex of chimeric molecules (amino acid sequences) in which each chimeric molecule combines a biologically active portion, such as the extracellular domain of each of the heteromultimeric receptor monomers, with a multimerization domain. The "multimerization domain" promotes stable interaction of the chimeric molecules within the heteromultimer complex. The multimerization domains may interact via an immunoglobulin sequence, leucine zipper, a hydrophobic region, a hydrophilic region, or a free thiol that forms an intermolecular disulfide bond between the chimeric molecules of the chimeric heteromultimer. The multimerization domain may comprise an immunoglobulin constant region. In addition a multimerization region may be engineered such that steric interactions not only promote stable interaction, but further promote the formation of heterodimers over homodimers from a mixture of monomers. "Protuberances" are constructed by replacing small amino acid side chains from the interface of the first polypeptide with larger side chains (e.g. tyrosine or tryptophan). Compensatory "cavities" of identical or similar size to the protuberances are optionally created on the interface of the second polypeptide by replacing large amino acid side chains with smaller ones (e.g. alanine or threonine). The immunoglobulin sequence preferably, but not necessarily, is an immunoglobulin constant domain. The immunoglobulin moiety in the chimeras of the present invention may be obtained from IgG1, $IgG_2$, $IgG_3$ or $IgG_4$ subtypes, IgA, IgE, IgD or IgM, but preferably $IgG_1$ or $IgG_3$.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. Specifically, the treatment may directly prevent, slow down or otherwise decrease the pathology of cellular degeneration or damage, such as the pathology of tumor cells in cancer treatment, or may render the cells more susceptible to treatment by other therapeutic agents.

"Steroidogenesis" is the hormonally induced, CAMP-mediated acute regulation of steroid hormone biosynthesis in "steroidogenic cells" characterized by the mobilization of cholesterol from cellular stores to the mitochondria outer membrane, and its translocation to the inner membrane where the conversion of cholesterol to pregnenolone occurs.

"Steroidogenic tissue" refers to tissue which produces steroidal hormones by the process of steroidogenesis. Examples include tissues of the adrenal gland, the reproductive organs, gut and respiratory tract tissue.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, other higher primates, domestic and farm animals, and zoo, sports, or pet animals, such as dogs, cats, cattle, horses, sheep, pigs, goats, rabbits, etc. Preferably, the mammal is human.

"Tumor", as used herein, refers to all neoplastic cell growth and proliferation, whether malignant or benign, and all precancerous and cancerous cells and tissues.

The terms "cancer" and "cancerous" refer to or describe the physiological condition in mammals that is typically characterized by unregulated cell growth. Examples of cancers of particular interest herein include cancers of the reproductive organs, e.g. ovarian cancer, testicular cancer, uterine cancer, cervical cancer; prostate cancer; cancers of the adrenal gland, including cancers of the adrenal cortex (e.g. adrenocortical carcinoma) and the adrenal medulla; thyroid cancer; parathyroid cancer; pancreatic cancer; and endometrial carcinoma.

The "pathology" of a disease includes all phenomena that compromise the well-being of the patient. For cancer, this includes, without limitation, abnormal or uncontrollable cell growth, metastasis, interference with the normal functioning of neighboring cells, release of cytokines or other secretory products at abnormal levels, suppression or aggravation of inflammatory or immunological response, etc.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™

A "liposome" is a small vesicle composed of various types of lipids, phospholipids and/or surfactant which is useful for delivery of a drug (such as a Bv8 polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

The terms "vascular endothelial growth factor", "VEGF", "VEGF polypeptide" and "VEGF protein" when used herein encompass native sequence VEGF and VEGF variants (which are further defined herein). The VEGF polypeptide may be isolated from a variety of sources, such as from human tissue types or from another source, or prepared by recombinant and/or synthetic methods.

A "native sequence VEGF" comprises a polypeptide having the same amino acid sequence as a VEGF derived from nature. Such native sequence VEGF can be isolated from nature or can be produced by recombinant and/or synthetic means. The term "native sequence VEGF" specifically encompasses naturally-occurring truncated or secreted forms (e.g., an extracellular domain sequence), naturally-occurring variant forms (e.g., alternatively spliced forms) and naturally-occurring allelic variants of the VEGF. In one embodiment of the invention, the native sequence VEGF is one of the five known isoforms, consisting of 121, 145, 165, 189, and 206 amino acid residues, respectively, as described, for example in U.S. Pat. Nos. 5,332,671 and 5,240,848; in PCT Publication No. WO 98/10071; Leung et al., *Science* 246:1306-1309 (1989); and Keck et al., *Science* 246:1309-1312 (1989).

"VEGF variant polypeptide" means an active VEGF polypeptide as defined below having at least about 80%, preferably at least about 85%, more preferably at least about 90%, event more preferably at least about 95%, most preferably at least about 98% amino acid sequence identity with the amino acid sequence of a native sequence VEGF. Such VEGF variant polypeptides include, for instance, VEGF polypeptides wherein one or more amino acid residues are added, or deleted, at the N- and/or C-terminus, as well as within one or more internal domains, of the native sequence.

The sequence identity (either amino acid or nucleic acid) for VEGF is determined using the same approach specifically described with regard to Bv8. Similarly, the definitions provided for agonist and antagonists of Bv8, including but not limited to antibodies, will apply to VEGF agonists and antagonists.

B. METHODS FOR CARRYING OUT THE INVENTION

1. Identification of Bv8 Variants

In addition to the full-length native sequence Bv8 polypeptides described herein, it is contemplated that Bv8 variants can be identified, prepared and used in the present invention. Bv8 variants can be prepared by introducing appropriate nucleotide changes into the Bv8 DNA, and/or by synthesis of the desired Bv8 polypeptide. Those skilled in the art will appreciate that amino acid changes may alter post-translational processes of the Bv8, such as changing the number or position of glycosylation sites. The methods of production of Bv8 variants are preferably the same as for native sequence Bv8 as described in detail below, the only difference being the substitution of the nucleic acid encoding the Bv8 variant for the nucleic acid encoding native sequence Bv8.

Nucleic acid molecules that encode Bv8 are used in the methods of the present invention. cDNAs encoding two full-length variants of human Bv8 are provided in FIGS. 1 and 2 (SEQ ID NOS: 1 and 2), and the corresponding deduced amino acid sequences are provided in FIGS. 2 and 4 (SEQ ID NOS: 2 and 4). A cDNA encoding mouse Bv8 is provided in FIG. 5 (SEQ ID NO: 5) and the corresponding deduced amino acid sequence is provided in FIG. 6 (SEQ ID NO: 6). The polynucleotides used in the present invention can be obtained using standard techniques well known to those skilled in the art such as, for example, hybridization screening and PCR methodology.

Any nucleotide sequence which encodes the amino acid sequence of Bv8 can be used to generate recombinant molecules which direct the expression of Bv8. Additionally, the methods of the present invention may also utilize a fusion polynucleotide between a Bv8 coding sequence and a second coding sequence for a heterologous protein.

In order to clone full length homologous cDNA sequences from any species encoding the entire Bv8 cDNA or to clone family members or variant forms such as allelic variants, labeled DNA probes made from fragments corresponding to any part of the cDNA sequences disclosed herein may be used to screen a cDNA library derived from a cell or tissue type believed to express Bv8. More specifically, oligonucleotides corresponding to either the 5' or 3' terminus of the coding sequence may be used to obtain longer nucleotide sequences.

It may be necessary to screen multiple cDNA libraries from different tissues to obtain a full-length cDNA. In the event that it is difficult to identify cDNA clones encoding the complete 5' terminal coding region, an often encountered situation in cDNA cloning, the RACE (Rapid Amplification of cDNA Ends) technique may be used. RACE is a proven PCR-based strategy for amplifying the 5' end of incomplete cDNAs. 5'-RACE-Ready RNA synthesized from human placenta containing a unique anchor sequence is commercially available (Clontech). To obtain the 5' end of the cDNA, PCR is carried out on 5'-RACE-Ready cDNA using the provided anchor primer and the 3' primer. A secondary PCR is then carried out using the anchored primer and a nested 3' primer according to the manufacturer's instructions. Once obtained, the full length cDNA sequence may be translated into amino acid sequence and examined for certain landmarks such as a continuous open reading frame flanked by translation initiation and termination sites, a potential signal sequence and finally overall structural similarity to the Bv8 sequences disclosed herein.

Alternatively, a labeled probe may be used to screen a genomic library derived from any organism of interest using appropriate stringent conditions as described infra.

Isolation of a Bv8 coding sequence or a homologous sequence may be carried out by the polymerase chain reactions (PCR) using two degenerate oligonucleotide primer pools designed on the basis of the Bv8 coding sequences disclosed herein. The template for the reaction may be cDNA obtained by reverse transcription (RT) of mRNA prepared from, for example, human or non-human cell lines or tissues known or suspected to express a Bv8 gene allele.

The PCR product may be subcloned and sequenced to ensure that the amplified sequences represent the sequences of a Bv8 coding sequence. The PCR fragment may then be used to isolate a full-length cDNA clone by a variety of methods. For example, the amplified fragment may be labeled and used to screen a bacteriophage cDNA library. Alternatively, the labeled fragment may be used to isolate genomic clones via the screening of a genomic library.

PCR technology may also be utilized to isolate full-length cDNA sequences. For example, RNA may be isolated, following standard procedures, from an appropriate cellular or tissue source. An RT reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated.

A cDNA clone of a mutant or allelic variant of the Bv8 gene may be isolated, for example, by using PCR. In this case, the first cDNA strand may be synthesized by hybridizing an oligo-dT oligonucleotide to mRNA isolated from tissue known or suspected to express Bv8 in an individual putatively carrying the mutant Bv8 allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant Bv8 allele to that of the normal Bv8 allele, the mutation(s) responsible for the loss or alteration of function of the mutant Bv8 gene product can be ascertained.

Alternatively, a genomic library can be constructed using DNA obtained from an individual suspected of or known to carry a mutant Bv8 allele, or a cDNA library can be constructed using RNA from a tissue known, or suspected, to express a mutant Bv8 allele. An unimpaired Bv8 gene or any suitable fragment thereof may then be labeled and used as a probe to identify the corresponding mutant Bv8 allele in such libraries. Clones containing the mutant Bv8 gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant Bv8 allele in an individual suspected of or known to carry such a mutant allele. In this manner, gene products made by the putatively mutant tissue may be expressed and screened using standard antibody screening techniques in conjunction with antibodies raised against the normal Bv8 gene product, as described, below.

As used herein, the terms nucleic acid, polynucleotide and nucleotide are interchangeable and refer to any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages.

The terms nucleic acid, polynucleotide and nucleotide also specifically include nucleic acids composed of bases other than the five biologically occurring bases (adenine, guanine, thymine, cytosine and uracil). For example, a polynucleotide of the invention might contain at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridin-e, 5-carboxymethylaminomethyl-uracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiour-acil, beta-D-mannosylqueosine, 5N-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3)w, and 2,6-diaminopurine.

Furthermore, a polynucleotide used in the invention may comprise at least one modified sugar moiety selected from the group including but not limited to arabinose, 2-fluoroarabinose, xylulose, and hexose.

It is not intended that the methods of the present invention be limited by the source of the polynucleotide. The polynucleotide can be from a human or non-human mammal, derived from any recombinant source, synthesized in vitro or by chemical synthesis. The nucleotide may be DNA or RNA and may exist in a double-stranded, single-stranded or partially double-stranded form.

Nucleic acids useful in the present invention include, by way of example and not limitation, oligonucleotides such as antisense DNAs and/or RNAs; ribozymes; DNA for gene therapy; DNA and/or RNA chimeras; various structural forms of DNA including single-stranded DNA, double-stranded DNA, supercoiled DNA and/or triple-helix DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, *Oligonucleotide Synthesis: A Practical Approach*, IRL Press, Oxford, England). RNAs may be produced in high yield via in vitro transcription using plasmids such as SP65 (Promega Corporation, Madison, Wis.).

Any mRNA transcript encoded by Bv8 nucleic acid sequences may be used in the methods of the present invention, including in particular, mRNA transcripts resulting from alternative splicing or processing of mRNA precursors.

In some circumstances, as where increased nuclease stability is desired, nucleic acids having modified internucleoside linkages may be preferred. Nucleic acids containing modified internucleoside linkages may also be synthesized using reagents and methods that are well known in the art. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide ($—CH_2—S—CH_2—$), dimethylene-sulfoxide ($—CH_2—SO—CH_2—$), dimethylene-sulfone ($—CH_2—SO_2—CH_2—$), 2'-O-alkyl, and 2'-deoxy-2'-fluoro phosphorothioate internucleoside linkages are well known in the art (see Uhlmann et al., 1990, *Chem. Rev.* 90:543-584; Schneider et al., 1990, *Tetrahedron Lett.* 31:335 and references cited therein).

In some embodiments of the present invention, the nucleotide used is an .alpha.-anomeric nucleotide. An .alpha.-anomeric nucleotide forms specific double-stranded hybrids with complementary RNA in which, contrary to the usual .beta.-units, the strands run parallel to each other (Gautier et al., 1987, *Nucl. Acids Res.* 15:6625-6641). The nucleotide is a 2N-0-methylribonucleotide (Inoue et al., 1987, Nucl. Acids Res. 15:6131-6148), or a chimeric RNA-DNA analogue (Inoue et al., 1987, FEBS Lett. 215:327-330).

The nucleic acids may be purified by any suitable means, as are well known in the art. For example, the nucleic acids can be purified by reverse phase or ion exchange HPLC, size exclusion chromatography or gel electrophoresis. Of course, the skilled artisan will recognize that the method of purification will depend in part on the size of the DNA to be purified.

Isolated or purified polynucleotides having at least 10 nucleotides (i.e., a hybridizable portion) of a Bv8 coding sequence or its complement may also be used in the methods of the present invention. In other embodiments, the polynucleotides contain at least 25 (continuous) nucleotides, 50 nucleotides, 100 nucleotides, 150 nucleotides, or 200 nucleotides of a Bv8 coding sequence, or a full-length Bv8 coding sequence. Nucleic acids can be single or double stranded. Additionally, the invention relates to polynucleotides that selectively hybridize to a complement of the foregoing coding sequences. In preferred embodiments, the polynucleotides contain at least 10, 25, 50, 100, 150 or 200 nucleotides or the entire length of a Bv8 coding sequence.

Nucleotide sequences that encode a mutant of Bv8, peptide fragments of Bv8, truncated forms of Bv8, and Bv8 fusion proteins may also be useful in the methods of the present invention. Nucleotides encoding fusion proteins may include, but are not limited to, full length Bv8 sequences, truncated forms of Bv8, or nucleotides encoding peptide fragments of Bv8 fused to an unrelated protein or peptide, such as for example, a domain fused to an Ig Fc domain which increases the stability and half life of the resulting fusion protein (e.g., Bv8-Ig) in the bloodstream; or an enzyme such as a fluorescent protein or a luminescent protein which can be used as a marker.

Furthermore, Bv8 polynucleotide variants that have been generated, at least in part, by some form of directed evolution, e.g., gene shuffling and/or recursive sequence recombination, described in U.S. Pat. Nos. 5,605,793 and 5,837,458, incorporated by reference herein in their entirety, may be used in the methods of the present invention. For example, using such techniques one can use an Bv8 encoding sequence, or a plurality of Bv8 encoding sequences, as the starting point for the generation of novel sequences encoding functionally and/or structurally similar proteins with altered functional and/or structural characteristics.

Highly related gene homologs of the Bv8 encoding polynucleotide sequences described above may also be useful in the present invention. Highly related gene homologs are polynucleotides encoding proteins that have at least about 60% amino acid sequence identity with the amino acid sequence of a naturally occurring Bv8 such as the mature human Bv8 of FIG. 2 or FIG. 4 (SEQ ID NOs: 2 and 4), preferably at least about 65%, 70%, 75%, 80%, with increasing preference of at least about 85% to at least about 99% amino acid sequence identity, in 1% increments. Highly related homologs can encode proteins sharing functional activities with Bv8.

The methods of the present invention also benefit by the use of (a) DNA vectors that contain any of the foregoing Bv8 coding sequences and/or their complements (i.e., antisense); (b) DNA expression vectors that contain any of the foregoing Bv8 coding sequences operatively associated with a regulatory element that directs the expression of the coding sequences; (c) genetically engineered host cells that contain any of the foregoing Bv8 coding sequences operatively associated with a regulatory element that directs the expression of the coding sequences in the host cell; and (d) genetically engineered host cells that express an endogenous Bv8 gene under the control of an exogenously introduced regulatory element (i.e., gene activation).

Variations in native sequence Bv8 or in various domains of the Bv8 described herein, can be made, for example, using any of the techniques and guidelines for conservative and non-conservative mutations set forth, for instance, in U.S. Pat. No. 5,364,934. Variations may be a substitution, deletion or insertion of one or more codons encoding Bv8 that results in a change in the amino acid sequence of the Bv8 as compared with native sequence Bv8. Optionally the variation is by substitution of at least one amino acid with any other amino acid in one or more of the domains of the Bv8. Guidance in determining which amino acid residue may be inserted, substituted or deleted without adversely affecting the desired activity may be found by comparing the sequence of Bv8 with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Bv8 polypeptide fragments are also useful in the methods of the present invention. Such fragments may be truncated at the N-terminus or C-terminus, or may lack internal residues, for example, when compared with a full-length native protein. Certain fragments lack amino acid residues that are not essential for a desired biological activity of the Bv8 polypeptide.

Bv8 fragments may be prepared by any of a number of conventional techniques. Desired peptide fragments may be chemically synthesized. An alternative approach involves generating Bv8 fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, Bv8 polypeptide fragments share at least one biological and/or immunological activity with a native Bv8 polypeptide.

In particular embodiments, conservative substitutions of interest are shown in Table I under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
|---|---|---|
| Ala(A) | val; leu; ile | val |
| Arg(R) | lys; gln; asn | lys |
| Asn(N) | gln; his; lys; arg | gln |
| Asp(D) | Glu | glu |
| Cys(C) | Ser | ser |
| Gln(Q) | Asn | asn |
| Glu(E) | Asp | asp |
| Gly(G) | pro; ala | ala |
| His(H) | asn; gln; lys; arg | arg |
| Ile(I) | leu; val; met; ala; phe; Norleucine | leu |
| Leu(L) | norleucine; ile; val; met; ala; phe | ile |
| Lys(K) | arg; gln; asn | arg |
| Met(M) | leu; phe; ile | leu |
| Phe(F) | leu; val; ile; ala; tyr | leu |
| Pro(P) | Ala | ala |
| Ser(S) | Thr | thr |
| Thr(T) | Ser | ser |
| Trp(W) | tyr; phe | tyr |
| Tyr(Y) | trp; phe; thr; ser | phe |
| Val(V) | ile; leu; met; phe; ala; norleucine | leu |

Substantial modifications in function or immunological identity of the Bv8 polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis (Carter et al., *Nucl. Acids Res.*, 13:4331 (1986); Zoller et al., Nucl. Acids Res., 10:6487 (1987)), cassette mutagenesis (Wells et al., *Gene,* 34:315 (1985)), restriction selection mutagenesis (Wells et al., *Philos. Trans. R. Soc. London SerA,* 317:415 (1986)) or other known techniques can be performed on cloned DNA to produce the Bv8 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant (Cunningham and Wells, *Science,* 244: 1081-1085 (1989)). Alanine is also typically preferred because it is the most common amino acid. Further, it is frequently found in both buried and exposed positions (Creighton, *The Proteins*, (W. H. Freeman & Co., N.Y.); Chothia, *J. Mol. Biol.,* 150:1 (1976)). If alanine substitution does not yield adequate amounts of variant, an isoteric amino acid can be used.

2. Production of Bv8 and Bv8 Variants

Techniques suitable for the production of Bv8 and Bv8 variants are well known in the art. Because the preferred techniques are the same for Bv8 and Bv8 variants, the techniques described below apply to Bv8 variants as well as to native sequence Bv8.

The preferred methods of production include isolating Bv8 from an endogenous source of the polypeptide, peptide synthesis (using a peptide synthesizer) and recombinant techniques (or any combination of these techniques).

Most of the discussion below pertains to recombinant production of Bv8 by culturing cells transformed with a vector containing Bv8 nucleic acid and recovering the polypeptide from the cell culture. However, one of skill in the art will recognize that there are many ways of producing Bv8.

Briefly, this method involves transforming primary human cells containing an Bv8-encoding gene with a construct (i.e., vector) comprising an amplifiable gene (such as dihydrofolate reductase (DHFR) or others discussed below) and at least one flanking region of a length of at least about 150 bp that is homologous with a DNA sequence at the locus of the coding region of the Bv8 gene to provide amplification of the Bv8 gene. The amplifiable gene must be at a site that does not interfere with expression of the Bv8 gene. The transformation is conducted such that the construct becomes homologously integrated into the genome of the primary cells to define an amplifiable region.

Primary cells comprising the construct are then selected for by means of the amplifiable gene or other marker present in the construct. The presence of the marker gene establishes the presence and integration of the construct into the host genome. No further selection of the primary cells need be made, since selection will be made in the second host. If desired, the occurrence of the homologous recombination event can be determined by employing PCR and either sequencing the resulting amplified DNA sequences or determining the appropriate length of the PCR fragment when DNA from correct homologous integrants is present and expanding only those cells containing such fragments. Also if desired, the selected cells may be amplified at this point by stressing the cells with the appropriate amplifying agent (such as methotrexate if the amplifiable gene is DHFR), so that multiple copies of the target gene are obtained. Preferably, however, the amplification step is not conducted until after the second transformation described below.

After the selection step, DNA portions of the genome, sufficiently large to include the entire amplifiable region, are isolated from the selected primary cells. Secondary mammalian expression host cells are then transformed with these genomic DNA portions and cloned, and clones are selected that contain the amplifiable region. The amplifiable region is then amplified by means of an amplifying agent if not already amplified in the primary cells. Finally, the secondary expression host cells now comprising multiple copies of the amplifiable region containing Bv8 are grown so as to express the gene and produce the protein.

The DNA encoding Bv8 may be obtained from any cDNA library prepared from tissue believed to possess the Bv8 mRNA and to express it at a detectable level. Accordingly, Bv8 DNA can be conveniently obtained from a cDNA library prepared, for example, from multiple human tissues. The Bv8-encoding gene may also be obtained from a genomic library or by oligonucleotide synthesis.

Libraries are screened with probes (such as antibodies to Bv8 or oligonucleotides of about 20-80 bases) designed to identify the gene of interest or the protein encoded by it. Screening the cDNA or genomic library with the selected probe may be conducted using standard procedures as described in chapters 10-12 of Sambrook et al., *Molecular Cloning: A Laboratory Manual* (New York: Cold Spring Harbor Laboratory Press, 1989). An alternative means to isolate the gene encoding Bv8 is to use PCR methodology as described in section 14 of Sambrook et al., supra.

A preferred method of isolating Bv8 cDNA is to use carefully selected oligonucleotide sequences to screen cDNA libraries from various human tissues. The oligonucleotide sequences selected as probes should be of sufficient length and sufficiently unambiguous that false positives are minimized. Preferred sequences are obtained from the naturally occurring Bv8 disclosed herein.

The oligonucleotide must be labeled such that it can be detected upon hybridization to DNA in the library being screened. The preferred method of labeling is to use $^{32}$P-labeled ATP with polynucleotide kinase, as is well known in the art, to radiolabel the oligonucleotide. However, other methods may be used to label the oligonucleotide, including, but not limited to, biotinylation or enzyme labeling.

The nucleic acid (e.g., cDNA or genomic DNA) encoding Bv8 is inserted into a replicable vector for further cloning (amplification of the DNA) or for expression. Many vectors are available. The vector components generally include, but are not limited to, one or more of the following: a signal sequence, an origin of replication, one or more marker genes, an enhancer element, a promoter, and a transcription termination sequence.

The Bv8 of this invention may be produced recombinantly not only directly, but also as a fusion polypeptide with a heterologous polypeptide, which is preferably a signal sequence or other polypeptide having a specific cleavage site at the N-terminus of the mature protein or polypeptide. In general, the signal sequence may be a component of the vector, or it may be a part of the Bv8 DNA that is inserted into the vector. The heterologous signal sequence selected preferably is one that is recognized and processed (i.e., cleaved by a signal peptidase) by the host cell. For prokaryotic host cells that do not recognize and process the native Bv8 signal sequence, the signal sequence is substituted by a prokaryotic signal sequence selected, for example, from the group consisting of the alkaline phosphatase, penicillinase, lpp, and heat-stable enterotoxin II leaders. For yeast secretion the native signal sequence may be substituted by, e.g., the yeast invertase leader, a-factor leader (including *Saccharomyces* and *Kluyveromyces* a-factor leaders, the latter described in U.S. Pat. No. 5,010,182 issued Apr. 23, 1991), or acid phosphatase leader, the *C. albicans* glucoamylase leader (EP 362, 179 published Apr. 4, 1990), or the signal described in WO 90/13646 published Nov. 15, 1990. In mammalian cell expression the native signal sequence (e.g., the Bv8 presequence that normally directs secretion of Bv8 from human cells in vivo) is satisfactory, although other mammalian signal sequences may be suitable, such as signal sequences from other animal Bv8 polypeptides, and signal sequences from secreted polypeptides of the same or related species, as well as viral secretory leaders, for example, the herpes simplex gD signal.

The DNA for such precursor region is ligated in reading frame to DNA encoding the mature Bv8 or a soluble variant thereof.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2µ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using *Bacillus* species as hosts, for example, by including in the vector a DNA sequence that is complementary to a sequence found in *Bacillus* genomic DNA. Transfection of *Bacillus* with this vector results in homologous recombination with the genome and insertion of Bv8 DNA. However, the recovery of genomic DNA encoding Bv8 is more complex than that of an exogenously replicated vector because restriction enzyme digestion is required to excise the Bv8 DNA.

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli.*

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin. Another example of suitable selectable markers for mammalian cells are those that enable the identification of cells competent to take up the Bv8 nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes Bv8. Amplification is the process by which genes in greater demand for the production of a protein critical for growth are reiterated in tandem within the chromosomes of successive generations of recombinant cells. Increased quantities of Bv8 are synthesized from the amplified DNA. Other examples of amplifiable genes include metallothionein-I and -II, preferably primate metallothionein genes, adenosine deaminase, ornithine decarboxylase, etc. A preferred vector system is provided in U.S. Pat. No. 5,561,053.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub et al., *Proc. Natl. Acad. Sci. USA,* 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding Bv8. This amplification technique can be used with any otherwise suitable host, e.g., ATCC No. CCL61 CHO—K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding Bv8, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature,* 282:39 (1979)). The trp1 gene provides a selection marker for a mutant strain of yeast lacking the ability to grow in tryptophan, for example, ATCC No. 44076 or PEP4-1. Jones, *Genetics,* 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μn circular plasmid pKD1 can be used for transformation of *Kluyveromyces* yeasts. Bianchi et al., *Curr. Genet.,* 12:185 (1987). More recently, an expression system for large-scale production of recombinant calf chymosin was reported for *K. lactis*. Van den Berg, *Bio/Technology,* 8:135 (1990). Stable multi-copy expression vectors for secretion of mature recombinant human serum albumin by industrial strains of *Kluyveromyces* have also been disclosed. Fleer et al., *Bio/Technology,* 9:968-975 (1991).

Expression and cloning vectors usually contain a promoter that is recognized by the host organism and is operably linked to the Bv8 nucleic acid. Promoters are untranslated sequences located upstream (5') to the start codon of a structural gene (generally within about 100 to 1000 bp) that control the transcription and translation of particular nucleic acid sequence, such as the Bv8 nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to Bv8-encoding DNA by removing the promoter from the source DNA by restriction enzyme digestion and inserting the isolated promoter sequence into the vector. Both the native Bv8 promoter sequence and many heterologous promoters may be used to direct amplification and/or expression of the Bv8 DNA. However, heterologous promoters are preferred, as they generally permit greater transcription and higher yields of Bv8 as compared to the native Bv8 promoter.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT (SEQ ID NO: 9) region where X may be any nucleotide. At the 3' end of most eukaryotic genes is an AATAAA (SEQ ID NO: 10) sequence that may be the signal for addition of the poly-A tail to the 3' end of the coding sequence. All of these sequences are suitably inserted into eukaryotic expression vectors.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly-A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.,* 255:2073 (1980)) or other glycolytic enzymes (Hess et al., *J. Adv. Enzyme Reg.,* 7:149 (1968); Holland, *Biochemistry,* 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Bv8 transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the Bv8 sequence, provided such promoters are compatible with the host cell systems.

The early and late promoters of the SV40 virus are conveniently obtained as an SV40 restriction fragment that also contains the SV40 viral origin of replication. Fiers et al., *Nature,* 273:113 (1978); Mulligan et al., *Science,* 209:1422-1427 (1980); Pavlakis et al., *Proc. Natl. Acad. Sci. USA,* 78:7398-7402 (1981). The immediate early promoter of the human cytomegalovirus is conveniently obtained as a HindIII E restriction fragment. Greenaway et al., *Gene,* 18:355-360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature,* 295:503-508 (1982) on expressing cDNA encoding immune interferon in monkey cells; Reyes et al., *Nature,* 297:598-601 (1982) on expression of human β-interferon cDNA in mouse cells under the control of a thymidine kinase promoter from herpes simplex virus; Canaani et al., Proc. Natl. Acad. Sci. USA, 79:5166-5170 (1982) on expression of the human interferon β1 gene in cultured mouse and rabbit cells; and Gorman et al., *Proc. Natl. Acad. Sci. USA,* 79:6777-6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

Transcription of a DNA encoding Bv8 by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc. Natl. Acad. Sci. USA,* 78:993 (1981)) and 3' (Lusky et al., *Mol. Cell. Bio.,* 3:1108 (1983)) to the transcription unit, within an intron (Banerji et al., *Cell,* 33:729 (1983)), as well as within the coding sequence itself. Osborne et al., *Mol. Cell. Bio.,* 4:1293 (1984). Many enhancer sequences are now known from mammalian genes (globin, elastase, albumin, a-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature,* 297: 17-18 (1982) on enhancing elements for activation of eukaryotic promoters. The enhancer may be spliced into the vector at a position 5' or 3' to the Bv8-encoding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding Bv8.

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform *E. coli* K$_{12}$ strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.,* 9:309 (1981) or by the method of Maxam et al., *Methods in Enzymology,* 65:499 (1980).

Particularly useful in the preparation of Bv8 and Bv8 variants are expression vectors that provide for the transient expression in mammalian cells of DNA encoding Bv8. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17-16.22. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of Bv8 that are biologically active Bv8.

Other methods, vectors, and host cells suitable for adaptation to the synthesis of Bv8 in recombinant vertebrate cell culture are described in Gething et al., *Nature,* 293:620-625 (1981); Mantei et al., *Nature,* 281:40-46 (1979); EP 117,060; and EP 117,058. A particularly useful plasmid for mammalian cell culture expression of Bv8 is pRK5 (EP 307,247) or pSV16B. WO 91/08291 published Jun. 13, 1991. Suitable host cells for cloning or expressing the DNA in the vectors herein are prokaryote, yeast, or higher eukaryote cells. Suitable prokaryotes for this purpose include eubacteria, such as Gram-negative or Gram-positive organisms, for example, Enterobacteriaceae such as *Escherichia,* e.g., *E. coli, Enterobacter, Erwinia, Klebsiella, Proteus, Salmonella,* e.g., *Salmonella typhimurium, Serratia,* e.g., *Serratia marcescans,* and *Shigella,* as well as *Bacilli* such as *B. subtilis* and *B. licheniformis* (e.g., *B. licheniformis* 41P disclosed in DD 266,710 published Apr. 12, 1989), *Pseudomonas* such as *P. aeruginosa,* and *Streptomyces.* One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. Strain W3110 is a particularly preferred host or parent host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 27C7. The complete genotype of 27C7 is tonAΔ ptr3 phoAΔE15 Δ(argF-lac)169 ompT Δ degP41kan$^r$. Strain 27C7 was deposited on Oct. 30, 1991 in the American Type Culture Collection as ATCC No. 55,244. Alternatively, the strain of *E. coli* having mutant periplasmic protease disclosed in U.S. Pat. No. 4,946,783 issued Aug. 7, 1990 may be employed.

In addition to prokaryotes, eukaryotic microbes such as filamentous fungi or yeast are suitable cloning or expression hosts for Bv8-encoding vectors. *Saccharomyces cerevisiae,* or common baker's yeast, is the most commonly used among lower eukaryotic host microorganisms. However, a number of other genera, species, and strains are commonly available and useful herein, such as *Schizosaccharomyces pombe* (Beach et al., *Nature,* 290:140 (1981); EP 139,383 published May 2, 1985); *Kluyveromyces* hosts (U.S. Pat. No. 4,943,529; Fleer et al., supra) such as, e.g., *K. lactic* (MW98-8C, CBS683, CBS4574; Louvencourt et al., *J. Bacteriol,* 131 (1983)), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., supra), *K. thermotolerans,* and *K. marxianus; yarrowia* (EP 402,226); *Pichia pastoris* (EP 183,070; Sreekrishna et al., *J. Basic Microbiol.,* 28:265-278 (1988)); *Candida; Trichoderma reesia* (EP 244,234); *Neurospora crassa* (Case et al., *Proc. Natl. Acad. Sci. USA,* 76:5259-5263 (1979)); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.,* 112: 284-289 (1983); Tilburn et al., *Gene,* 26:205-221 (1983); Yelton et al., *Proc. Natl. Acad. Sci. USA,* 81:1470-1474 (1984)) and *A. niger.* Kelly et al., *EMBO J.,* 4:475-479 (1985).

Suitable host cells for the expression of glycosylated Bv8 are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology,* 6:47-55 (1988); Miller et al., in Genetic Engineering, Setlow et al., eds., Vol. 8 (Plenum Publishing, 1986), pp. 277-279; and Maeda et al., *Nature,* 315:592-594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens,* which has been previously manipulated to contain the Bv8-encoding DNA. During incubation of the plant cell culture with *A. tumefaciens,* the DNA encoding the Bv8 is transferred to the plant cell host such that it is transfected, and will, under appropriate conditions, express the Bv8-encoding DNA. In addition, regulatory and signal sequences compatible with plant cells are available, such as the nopaline synthase promoter and polyadenylation signal sequences. Depicker et al., *J. Mol. Appl. Gen.,* 1:561 (1982). In addition, DNA segments isolated from the upstream region of the T-DNA 780 gene are capable of activating or increasing transcription levels of plant-expressible genes in recombinant DNA-containing plant tissue. EP 321, 196 published Jun. 21, 1989.

However, interest has been greatest in vertebrate cells, and propagation of vertebrate cells in culture (tissue culture) has become a routine procedure. See, e.g., *Tissue Culture*, Academic Press, Kruse and Patterson, editors (1973). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.,* 36:59 (1977)); baby hamster kidney cells (BHK, ATCC CCL 10); Chinese hamster ovary cells/−DHFR (CHO, Urlaub et al., *Proc. Natl. Acad. Sci. USA,* 77:4216 (1980)); mouse sertoli cells (TM4, Mather, *Biol. Reprod,* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.,* 383:44-68 (1982)); MRC 5 cells; FS4 cells; and a human hepatoma line (Hep G2).

Host cells are transfected and preferably transformed with the above-described expression or cloning vectors for Bv8 production and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene,* 23:315 (1983) and WO 89/05859 published Jun. 29, 1989. In addition, plants may be transfected using ultrasound treatment as described in WO 91/00358 published 10 Jan. 1991.

For mammalian cells without such cell walls, the calcium phosphate precipitation method of Graham et al., *Virology,* 52:456-457 (1978) is preferred. General aspects of mammalian cell host-system transformations have been described in U.S. Pat. No. 4,399,216 issued 16 Aug., 1983. Transformations into yeast are typically carried out according to the method of Van Solingen et al., *J. Bact.,* 130:946 (1977) and Hsiao et al., *Proc. Natl. Acad. Sci. USA,* 76:3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology,* 185:527-537 (1990) and Mansour et al., *Nature,* 336:348-352 (1988).

Prokaryotic cells used to produce Bv8 polypeptide are cultured in suitable media as described generally in Sambrook et al., supra.

The mammalian host cells used to produce the Bv8 of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al. *Meth. Enz.,* 58:44 (1979), Barnes et al., *Anal. Biochem.,* 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: a Practical Approach*, M. Butler, ed. (IRL Press, 1991).

The host cells referred to in this disclosure encompass cells in culture as well as cells that are within a host animal.

Gene amplification and/or expression may be measured in a sample directly, for example, by conventional Southern blotting, Northern blotting to quantitate the transcription of mRNA (Thomas, *Proc. Natl. Acad. Sci. USA,* 77:5201-5205 (1980)), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, can be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75:734-738 (1980).

Antibodies useful for immunohistochemical staining and/or assay of sample fluids may be either monoclonal or polyclonal, and may be prepared as described herein.

Bv8 preferably is recovered from the culture medium as a secreted polypeptide, although it also may be recovered from host cell lysates. If the Bv8 is membrane-bound, it can be released from the membrane using a suitable detergent solution (e.g. Triton-X 100).

When Bv8 is produced in a recombinant cell other than one of human origin, the Bv8 is completely free of proteins or polypeptides of human origin. However, it is necessary to purify Bv8 from recombinant cell proteins or polypeptides to obtain preparations that are substantially homogeneous as to Bv8. As a first step, the culture medium or lysate can be centrifuged to remove particulate cell debris. Bv8 can then be purified from contaminant soluble proteins and polypeptides with the following procedures, which are exemplary of suitable purification procedures: by fractionation on an ion-exchange column; ethanol precipitation; reverse phase HPLC; chromatography on silica; chromatofocusing; immunoaffinity; epitope-tag binding resin; SDS-PAGE; ammonium sulfate precipitation; gel filtration using, for example, Sephadex G-75; and protein A Sepharose columns to remove contaminants such as IgG.

3. Modifications of Bv8

Covalent modifications of Bv8 and Bv8 variants are included within the scope of this invention. One type of covalent modification includes reacting targeted amino acid residues of a Bv8 polypeptide with an organic derivatizing agent that is capable of reacting with selected side chains or the N- or C-terminal residues of the Bv8. Derivatization with bifunctional agents is useful, for instance, for crosslinking Bv8 to a water-insoluble support matrix or surface for use in the method for purifying anti-Bv8 antibodies, and vice versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the .alpha.-amino groups of lysine, arginine, and histidine side chains (T. E. Creighton, *Proteins: Structure and Molecular Properties*, W. H. Freeman & Co., San Francisco, pp. 79-86 (1983)), acetylation of the N-terminal amine, and amidation of any C-terminal carboxyl group.

Another type of covalent modification of the Bv8 polypeptide included within the scope of this invention comprises altering the native glycosylation pattern of the polypeptide. "Altering the native glycosylation pattern" is intended for purposes herein to mean deleting one or more carbohydrate moieties found in native sequence Bv8 (either by removing the underlying glycosylation site or by deleting the glycosylation by chemical and/or enzymatic means), and/or adding one or more glycosylation sites that are not present in the native sequence Bv8. In addition, the phrase includes qualitative changes in the glycosylation of the native proteins, involving a change in the nature and proportions of the various carbohydrate moieties present.

Addition of glycosylation sites to the Bv8 polypeptide may be accomplished by altering the amino acid sequence. The alteration may be made, for example, by the addition of, or substitution by, one or more serine or threonine residues to the native sequence Bv8 (for O-linked glycosylation sites). The Bv8 amino acid sequence may optionally be altered through changes at the DNA level, particularly by mutating the DNA encoding the Bv8 polypeptide at pre-selected bases such that codons are generated that will translate into the desired amino acids.

Another means of increasing the number of carbohydrate moieties on the Bv8 polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the Bv8 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of Bv8 comprises linking the Bv8 polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337.

The Bv8 of the present invention may also be modified in a way to form a chimeric molecule comprising Bv8 fused to another, heterologous polypeptide or amino acid sequence.

In one embodiment, such a chimeric molecule comprises a fusion of the Bv8 with a tag polypeptide that provides an epitope to which an anti-tag antibody can selectively bind. The epitope tag is generally placed at the amino- or carboxyl-terminus of the Bv8. The presence of such epitope-tagged forms of the Bv8 can be detected using an antibody against the tag polypeptide. Also, provision of the epitope tag enables the Bv8 to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flue HA tag polypeptide and its antibody 12CA5 (Field et al., *Mol. Cell. Biol.*, 8:2159-2165 (1988)); the c-myc tag and the 8F9, 3C7, 6E10, G4, B7 and 9E10 antibodies thereto (Evan et al., *Molecular and Cellular Biology*, 5:3610-3616 (1985)); and the *Herpes Simplex* virus glycoprotein D (gD) tag and its antibody (Paborsky et al., *Protein Engineering*, 3(6):547-553 (1990)). Other tag polypeptides include the Flag-peptide (Hopp et al., BioTechnology, 6:1204-1210 (1988)); the KT3 epitope peptide (Martin et al., *Science*, 255:192-194 (1992)); an .alpha.-tubulin epitope peptide (Skinner et al., *J. Biol. Chem.*, 266:15163-15166 (1991)); and the T7 gene 10 protein peptide tag (Lutz-Freyermuth et al., *Proc. Natl. Acad. Sci. USA*, 87:6393-6397 (1990)).

In an alternative embodiment, the chimeric molecule may comprise a fusion of Bv8 with an immunoglobulin or a particular region of an immunoglobulin. For a bivalent form of the chimeric molecule (also referred to as an "immunoadhesin"), such a fusion could be to the Fc region of an IgG molecule.

The simplest and most straightforward immunoadhesin design combines the binding region(s) of the "adhesin" protein with the hinge and Fc regions of an immunoglobulin heavy chain. Ordinarily, when preparing Bv8-immunoglobulin chimeras for use in the present invention, nucleic acid encoding Bv8 will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge and CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain.

The precise site at which the fusion is made is not critical; particular sites are well known and may be selected in order to optimize the biological activity of the Bv8-immunoglobulin chimeras.

In some embodiments, the Bv8-immunoglobulin chimeras are assembled as monomers, or hetero- or homo-multimer, and particularly as dimers or tetramers, essentially as illustrated in WO 91/08298.

In a preferred embodiment, the Bv8 sequence is fused to the N-terminus of the C-terminal portion of an antibody (in particular the Pc domain), containing the effector functions of an immunoglobulin, e.g. immunoglobulin $G_1$ (IgG1). It is possible to fuse the entire heavy chain constant region to the Bv8 sequence. However, more preferably, a sequence beginning in the hinge region just upstream of the papain cleavage site (which defines IgG Fc chemically; residue 216, taking the first residue of heavy chain constant region to be 114, or analogous sites of other immunoglobulins) is used in the fusion. In a particularly preferred embodiment, the Bv8 amino acid sequence is fused to the hinge region and CH2 and CH3, or to the CH1, hinge, CH2 and CH3 domains of an IgG1, IgG2, or IgG3 heavy chain. The precise site at which the fusion is made is not critical, and the optimal site can be determined by routine experimentation.

In some embodiments, the Bv8-immunoglobulin chimeras are assembled as multimer, and particularly as homo-dimers or -tetramers. Generally, these assembled immunoglobulins will have known unit structures. A basic four chain structural unit is the form in which IgG, IgD, and IgE exist. A four-unit is repeated in the higher molecular weight immunoglobulins; IgM generally exists as a pentamer of basic four-units held together by disulfide bonds. IgA globulin, and occasionally IgG globulin, may also exist in multimeric form in serum. In the case of a multimer, each four-unit may be the same or different.

Alternatively, the Bv8 sequence can be inserted between immunoglobulin heavy chain and light chain sequences such that an immunoglobulin comprising a chimeric heavy chain is obtained. In this embodiment, the Bv8 sequence is fused to the 3' end of an immunoglobulin heavy chain in each arm of an immunoglobulin, either between the hinge and the CH2 domain, or between the CH2 and CH3 domains. Similar constructs have been reported by Hoogenboom et al., *Mol. Immunol.*, 28:1027-1037 (1991).

Although the presence of an immunoglobulin light chain is not required in the immunoadhesins of the present invention, an immunoglobulin light chain might be present either covalently associated to a Bv8-immunoglobulin heavy chain fusion polypeptide, or directly fused to Bv8. In the former case, DNA encoding an immunoglobulin light chain is typically coexpressed with the DNA encoding the Bv8-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567 issued 28 Mar. 1989.

In a preferred embodiment, the immunoglobulin sequences used in the construction of the immunoadhesins of the present invention are from an IgG immunoglobulin heavy chain constant domain. For human immunoadhesins, the use of human IgG1 and IgG3 immunoglobulin sequences is preferred. A major advantage of using IgG1 is that IgG1 immunoadhesins can be purified efficiently on immobilized protein A. In contrast, purification of IgG3 requires protein G, a significantly less versatile medium. However, other structural and functional properties of immunoglobulins should be considered when choosing the Ig fusion partner for a particular immunoadhesin construction. For example, the IgG3 hinge is longer and more flexible, so it can accommodate larger adhesin domains that may not fold or function properly when fused to IgG1. Another consideration may be valency; IgG immunoadhesins are bivalent homodimers, whereas Ig subtypes like IgA and IgM may give rise to dimeric or pentameric structures, respectively, of the basic Ig homodimer unit. For Bv8 immunoadhesins designed for in vivo application, the pharmacokinetic properties and the effector functions specified by the Fc region are important as well. Although IgG1, IgG2 and IgG4 all have in vivo half-lives of 21 days, their relative potencies at activating the complement system are different. IgG4 does not activate complement, and IgG2 is significantly weaker at complement activation than IgG1. Moreover, unlike IgG1, IgG2 does not bind to Fc receptors on mononuclear cells or neutrophils. While IgG3 is optimal for complement activation, its in vivo half-life is approximately one third of the other IgG isotypes. Another important consideration for immunoadhesins designed to be used as human therapeutics is the number of allotypic variants of the particular isotype. In general, IgG isotypes with fewer serologically-defined allotypes are preferred. For example, IgG1 has only four serologically-defined allotypic sites, two of which (G1m and 2) are located in the Fc region; and one of these sites G1m1, is non-immunogenic. In contrast, there are 12 serologically-defined allotypes in IgG3, all of which are in the Fc region; only three of these sites (G3 m5, 11 and 21) have one allotype which is nonimmunogenic. Thus, the potential immunogenicity of a .gamma.3 immunoadhesin is greater than that of a γ1 immunoadhesin.

With respect to the parental immunoglobulin, a useful joining point is just upstream of the cysteines of the hinge that form the disulfide bonds between the two heavy chains. In a frequently used design, the codon for the C-terminal residue of the Bv8 part of the molecule is placed directly upstream of the codons for the sequence DKTHTCPPCP (SEQ ID NO: 11) of the IgG1 hinge region.

The general methods suitable for the construction and expression of immunoadhesins are the same as those disclosed hereinabove with regard to Bv8. Bv8 immunoadhesins are most conveniently constructed by fusing the cDNA sequence encoding the Bv8 portion in-frame to an Ig cDNA sequence. However, fusion to genomic Ig fragments can also be used (see, e.g., Gascoigne et al., *Proc. Natl. Acad. Sci. USA*, 84:2936-2940 (1987); Aruffo et al., *Cell*, 61:1303-1313 (1990); Stamenkovic et al., *Cell*, 66:1133-1144 (1991)). The latter type of fusion requires the presence of Ig regulatory sequences for expression. cDNAs encoding IgG heavy-chain constant regions can be isolated based on published sequence from cDNA libraries derived from spleen or peripheral blood lymphocytes, by hybridization or by polymerase chain reaction (PCR) techniques. The cDNAs encoding the Bv8 and Ig parts of the immunoadhesin are inserted in tandem into a plasmid vector that directs efficient expression in the chosen host cells. For expression in mammalian cells, pRK5-based vectors (Schall et al., *Cell*, 61:361-370 (1990)) and CDM8-based vectors (Seed, *Nature*, 329:840 (1989)) can be used. The exact junction can be created by removing the extra sequences between the designed junction codons using oligonucleotide-directed deletional mutagenesis (Zoller et al., *Nucleic Acids Res.*, 10:6487 (1982); Capon et al., *Nature*, 337:525-531 (1989)). Synthetic oligonucleotides can be used, in which each half is complementary to the sequence on either side of the desired junction; ideally, these are 36 to 48-mers. Alternatively, PCR techniques can be used to join the two parts of the molecule in-frame with an appropriate vector.

The choice of host cell line for the expression of Bv8 immunoadhesins depends mainly on the expression vector. Another consideration is the amount of protein that is required. Milligram quantities often can be produced by transient transfections. For example, the adenovirus EIA-transformed 293 human embryonic kidney cell line can be transfected transiently with pRK5-based vectors by a modification of the calcium phosphate method to allow efficient immunoadhesin expression. CDM8-based vectors can be used to transfect COS cells by the DEAE-dextran method (Aruffo et al., *Cell*, 61:1303-1313 (1990); Zettmeissl et al., *DNA Cell Biol. US*, 9:347-353 (1990)). If larger amounts of protein are desired, the immunoadhesin can be expressed after stable transfection of a host cell line. For example, a pRK5-based vector can be introduced into Chinese hamster ovary (CHO) cells in the presence of an additional plasmid encoding dihydrofolate reductase (DHFR) and conferring resistance to G418. Clones resistant to G418 can be selected in culture; these clones are grown in the presence of increasing levels of DHFR inhibitor methotrexate; clones are selected, in which the number of gene copies encoding the DHFR and immunoadhesin sequences is co-amplified. If the immunoadhesin contains a hydrophobic leader sequence at its N-terminus, it is likely to be processed and secreted by the transfected cells. The expression of immunoadhesins with more complex structures may require uniquely suited host cells; for example, components such as light chain or J chain may be provided by certain myeloma or hybridoma cell hosts (Gascoigne et al., 1987, supra, Martin et al., *J. Virol*, 67:3561-3568 (1993)).

Immunoadhesins can be conveniently purified by affinity chromatography. The suitability of protein A as an affinity ligand depends on the species and isotype of the immunoglobulin Fc domain that is used in the chimera. Protein A can be used to purify immunoadhesins that are based on human γ1, γ2, or γ4 heavy chains (Lindmark et al., *J. Immunol. Meth.*, 62:1-13 (1983)). Protein G is recommended for all mouse isotypes and for human γ3 (Guss et al., *EMBO J*, 5:1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. The conditions for binding an immunoadhesin to the protein A or G affinity column are dictated entirely by the characteristics of the Fc domain; that is, its species and isotype. Generally, when the proper ligand is chosen, efficient binding occurs directly from unconditioned culture fluid. One distinguishing feature of immunoadhesins is that, for human .gamma.1 molecules, the binding capacity for protein A is somewhat diminished relative to an antibody of the same Fc type. Bound immunoadhesin can be efficiently eluted either at acidic pH (at or above 3.0), or in a neutral pH buffer containing a mildly chaotropic salt. This affinity chromatography step can result in an immunoadhesin preparation that is >95% pure.

Other methods known in the art can be used in place of, or in addition to, affinity chromatography on protein A or G to purify immunoadhesins. Immunoadhesins behave similarly to antibodies in thiophilic gel chromatography (Hutchens et al., *Anal. Biochem.*, 159:217-226 (1986)) and immobilized metal chelate chromatography (Al-Mashikhi et al., *J. Dairy Sci.*, 71:1756-1763 (1988)). In contrast to antibodies, however, their behavior on ion exchange columns is dictated not only by their isoelectric points, but also by a charge dipole that may exist in the molecules due to their chimeric nature.

If desired, the immunoadhesins can be made bispecific. Thus, the immunoadhesins of the present invention may combine a Bv8 domain and a domain, such as a domain from another growth factor. For bispecific molecules, trimeric molecules, composed of a chimeric antibody heavy chain in one arm and a chimeric antibody heavy chain-light chain pair in the other arm of their antibody-like structure are advantageous, due to ease of purification. In contrast to antibody-producing quadromas traditionally used for the production of bispecific immunoadhesins, which produce a mixture often tetramers, cells transfected with nucleic acid encoding the three chains of a trimeric immunoadhesin structure produce a mixture of only three molecules, and purification of the desired product from this mixture is correspondingly easier.

4. Preparation and Identification of Modulators of Bv8 Activity

The present invention also encompasses methods of screening compounds to identify those that mimic or enhance one or more biological activity of Bv8 (agonists) or prevent the effect of Bv8 (antagonists). Bv8 agonists and antagonists are also referred to as Bv8 modulators. Screening assays for antagonist drug candidates are designed to identify compounds that bind or complex with Bv8 polypeptides, or otherwise interfere with the interaction of Bv8 with other cellular proteins.

a. Small Molecule Screening

Small molecules may have the ability to act as Bv8 agonists or antagonists and thus to be therapeutically useful. Such small molecules may include naturally occurring small molecules, synthetic organic or inorganic compounds and peptides. However, small molecules in the present invention are not limited to these forms. Extensive libraries of small molecules are commercially available and a wide variety of assays are well known in the art to screen these molecules for the desired activity.

Candidate Bv8 agonist or antagonist small molecules are preferably identified first in an assay that allows for the rapid identification of potential modulators of Bv8 activity. An example of such an assay is a protein-protein binding assay wherein the ability of the candidate molecule to bind to a Bv8 receptor is measured. In another example, the ability of candidate molecules to interfere with Bv8 binding to a Bv8 receptor is measured.

In a preferred embodiment, small molecule Bv8 agonists are identified by their ability to mimic one or more of the biological activities of Bv8. For example, small molecules are screened for their ability to induce proliferation of endothelial cells, to promote endothelial cell survival, as described in examples 2 and 3 below or to induce angiogenesis, as described in example 4 below.

In another embodiment, small molecule Bv8 antagonists are identified by their ability to inhibit one or more of the biological activities of Bv8. Thus a candidate compound is contacted with Bv8. The biological activity of the Bv8 is then assessed. In one embodiment the ability of the Bv8 to stimulate endothelial cell proliferation is determined, for example as described in Example 2. In another embodiment the ability of the Bv8 to promote endothelial cell survival is determined, for example as described in Example 3. A compound is identified as an antagonist where the biological activity of Bv8 is inhibited.

Compounds identified as Bv8 agonists or antagonists may be used in the methods of the present invention. For example Bv8 antagonists may be used to treat cancer.

b. Preparation and Identification of Agonist Antibodies

Agonist human and non-human polyclonal and monoclonal antibodies (including humanized forms of non-human monoclonal antibodies) which mimic the biological properties of Bv8 are also contemplated in the present invention. These include amino acid sequence variants, glycosylation variants and fragments of antibodies. General techniques for the production of such antibodies and the selection of agonist antibodies are known in the art and are briefly described below.

(i) Polyclonal Antibodies

Methods of preparing polyclonal antibodies are known in the art. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. It may be useful to conjugate the immunizing agent to a protein known to be immunogenic in the mammal being immunized, such as serum albumin, or soybean trypsin inhibitor. Examples of adjuvants that may be employed include Freund's complete adjuvant and MPL-TDM.

(ii) Monoclonal Antibodies

Monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103, (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), conditions under which the growth of HGPRT-deficient cells is prevented.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol,* 133:3001 (1984); Brodeur et al., *Monoclonal Antibody Production Techniques and Applications*, pp. 51-63, Marcel Dekker, Inc., New York, (1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.,* 107:220 (1980).

After hybridoma cells are identified that produce antibodies of the desired specificity, affinity, and/or activity, the cells may be subcloned by limiting dilution procedures and grown by standard methods (Goding, *Monoclonal Antibodies: Principles and Practice*, pp. 59-103 (Academic Press, 1986)). Suitable culture media for this purpose include, for example, DMEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., *Proc. Nat. Acad. Sci. U.S.A.,* 81:6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of a Bv8 agonist monoclonal antibody described herein.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

Recombinant production of antibodies will be described in more detail below.

(iii) Humanized Antibodies

Generally, a humanized antibody has one or more amino acid residues introduced into it from a non-human source. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239: 1534-1536 (1988)), by substituting rodent CDRs or CDR sequences for the corresponding sequences of a human antibody.

Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed Aug. 21, 1992, which is a continuation-in-part of application Ser. No. 07/715,272 filed Jun. 14, 1991.

(iv) Human Antibodies

Human monoclonal antibodies can be made by the hybridoma method. Human myeloma and mouse-human heteromyeloma cell lines for the production of human monoclonal antibodies have been described, for example, by Kozbor, *J. Immunol.* 133, 3001 (1984), and Brodeur, et al., *Monoclonal Antibody Production Techniques and Applications*, pages 51-63 (Marcel Dekker, Inc., New York, 1987).

It is now possible to produce transgenic animals (e.g. mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., *Proc. Natl. Acad. Sci. USA* 90, 2551-255 (1993); Jakobovits et al., *Nature* 362, 255-258 (1993).

Mendez et al. (*Nature Genetics* 15:146-156 (1997)) have further improved the technology and have generated a line of transgenic mice designated as "Xenomouse II" that, when challenged with an antigen, generates high affinity fully human antibodies. This was achieved by germ-line integration of megabase human heavy chain and light chain loci into mice with deletion into endogenous $J_H$ segment as described above. The Xenomouse II harbors 1,020 kb of human heavy chain locus containing approximately 66 $V_H$ genes, complete $D_H$ and $J_H$ regions and three different constant regions (μ, δ and χ), and also harbors 800 kb of human P locus containing 32 VP genes, JP segments and CP genes. The antibodies produced in these mice closely resemble that seen in humans in all respects, including gene rearrangement, assembly, and repertoire. The human antibodies are preferentially expressed over endogenous antibodies due to deletion in endogenous $J_H$ segment that prevents gene rearrangement in the murine locus.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as Ml3 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g. Johnson, Kevin S, and Chiswell, David J., *Current Opinion in Structural Biology* 3:564-571 (1993). Several sources of V-gene segments can be used for phage display. Clackson et al., *Nature* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., *Bio/Technol.* 10:779-783 [1992]). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires (also known as "the mother-of-all libraries") has been described by Waterhouse et al., *Nucl. Acids Res.* 21:2265-2266 (1993), and the isolation of a high affinity human antibody directly from such large phage library is reported by Griffith et al., *EMBO J.* (1994), in press. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable domains capable of restoring a functional antigen-binding site, i.e. the epitope governs (imprints) the choice of partner. When the process is repeated in order to replace the remaining rodent V domain, a human antibody is obtained (see PCT patent application WO 93/06213, published Apr. 1, 1993). Unlike traditional humanization of rodent antibodies by CDR grafting, this technique provides completely human antibodies, which have no framework or CDR residues of rodent origin.

(v) Bispecific Antibodies

Bispecific antibodies are monoclonal, preferably human or humanized, antibodies that have binding specificities for at least two different antigens. Methods for making bispecific antibodies are known in the art. Traditionally, the recombinant production of bispecific antibodies is based on the coexpression of two immunoglobulin heavy chain-light chain pairs, where the two heavy chains have different specificities (Millstein and Cuello, *Nature* 305, 537-539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published 13 May 1993), and in Traunecker et al., *EMBO* 10, 3655-3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in PCT Publication No. WO 94/04690, published on Mar. 3, 1994.

For further details of generating bispecific antibodies see, for example, Suresh et al., *Methods in Enzymology* 121, 210 (1986).

(vi) Heteroconjugate Antibodies

Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

(vii) Antibody Fragments

In certain embodiments, the Bv8 agonist antibody (including murine, human and humanized antibodies and antibody variants) is an antibody fragment. Various techniques have been developed for the production of antibody fragments. Traditionally, these fragments were derived via proteolytic digestion of intact antibodies (see, e.g., Morimoto et al., *J. Biochem. Biophys. Methods* 24:107-117 (1992) and Brennan et al., *Science* 229:81 (1985)). However, these fragments can now be produced directly by recombinant host cells. For example, Fab'-SH fragments can be directly recovered from *E. coli* and chemically coupled to form F(ab')$_2$ fragments (Carter et al, Bio/Technology 10:163-167 (1992)). In another embodiment, the F(ab')$_2$ is formed using the leucine zipper GCN4 to promote assembly of the F(ab')$_2$ molecule. According to another approach, Fv, Fab or F(ab')$_2$ fragments can be isolated directly from recombinant host cell culture. Other techniques for the production of antibody fragments will be apparent to the skilled practitioner.

(viii) Identification of Agonist Antibodies

Bv8 agonist antibodies are identified based on their biological activity. In one embodiment, Bv8 agonist antibodies are identified by their ability to induce proliferation of endothelial cells, as described in Example 2. In another embodiment, Bv8 agonist antibodies are identified by their ability to induce angiogenesis, as described in Example 5. Screening Assays for Proteins that Interact with Bv8

Any method suitable for detecting protein-protein interactions may be employed for identifying proteins or other molecules, including but not limited to transmembrane or intracellular proteins, that interact with Bv8. Among the traditional methods that may be employed are co-immunoprecipitation, crosslinking and co-purification through gradients or chromatographic columns to identify proteins that interact with Bv8. For such assays, the Bv8 component can be a full-length protein, a soluble derivative thereof, a peptide corresponding to a domain of interest, or a fusion protein containing some region of Bv8.

Methods may be employed which result in the simultaneous identification of genes that encode proteins capable of interacting with Bv8. These methods include, for example, probing expression libraries, in a manner similar to the well-known technique of antibody probing of 8gt11 libraries, using labeled Bv8 or a variant thereof.

A method that detects protein interactions in vivo, the two-hybrid system, is described in detail for illustration only and not by way of limitation. One version of this system has been described (Chien et al., 1991, *Proc. Natl. Acad. Sci. USA*, 88:9578-9582) and is commercially available from Clontech (Palo Alto, Calif.).

Briefly, utilizing such a system, plasmids are constructed that encode two hybrid proteins: one plasmid consists of nucleotides encoding the DNA-binding domain of a transcription activator protein fused to a nucleotide sequence encoding Bv8, or a polypeptide, peptide, or fusion protein therefrom, and the other plasmid consists of nucleotides encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., FIBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, Bv8 can be used as the bait gene product. Total genomic or cDNA sequences are fused to the DNA encoding an activation domain. This library and a plasmid encoding a hybrid of a bait Bv8 gene product fused to the DNA-binding domain are cotransformed into a yeast reporter strain, and the resulting transformants are screened for those that express the reporter gene. For example, and not by way of limitation, a bait Bv8 gene sequence, e.g., the genes open reading frame, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with the bait Bv8 gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait Bv8 gene-GAL4 fusion plasmid into a yeast strain that contains a lacZ gene driven by a promoter which contains a GAL4 activation sequence. A cDNA encoded protein, fused to GAL4 transcriptional activation domain, that interacts with the bait Bv8 gene product will reconstitute an active GAL4 protein and thereby drive expression. Colonies that drive expression can be detected by methods routine in the art. The cDNA can then be purified from these strains, and used to produce and isolate the bait Bv8 gene-interacting protein using techniques routinely practiced in the art.

a. Assays for Compounds that Modulate Bv8 Expression or Activity

The following assays are designed to identify compounds that interact with (e.g., bind to) Bv8, compounds that interfere with the interaction of Bv8 with its binding partners, cognate or receptor, and to compounds that modulate the activity of Bv8 gene expression (i.e., modulate the level of Bv8 gene expression) or modulate the levels of Bv8 in the body. Assays may additionally be utilized which identify compounds that bind to Bv8 gene regulatory sequences (e.g., promoter sequences) and, consequently, may modulate Bv8 gene expression. See, e.g., Platt, K. A., 1994, *J. Biol. Chem.* 269: 28558-28562, which is incorporated herein by reference in its entirety.

The compounds which may be screened in accordance with the invention include, but are not limited to peptides, antibodies and fragments thereof, and other organic compounds (e.g., peptidomimetics) that bind to an Bv8 or a Bv8 receptor and either mimic the activity triggered by a natural ligand (i.e., agonists) or inhibit the activity triggered by the natural ligand (i.e., antagonists).

Such compounds may include, but are not limited to, peptides such as, for example, soluble peptides, including but not limited to members of random peptide libraries; (see, e.g., Lam, K. S. et al., 1991, Nature 354:82-84; Houghten, R. et al., 1991, *Nature* 354:84-86), and combinatorial chemistry-derived molecular library made of D- and/or L-configuration amino acids, phosphopeptides (including, but not limited to members of random or partially degenerate, directed phosphopeptide libraries; see, e.g., Songyang, Z. et al., 1993, *Cell* 72:767-778), antibodies (including, but not limited to, polyclonal, monoclonal, humanized, anti-idiotypic, chimeric or single chain antibodies, and FAb, F(abN)$_2$ and FAb expression library fragments, and epitope-binding fragments thereof), and small organic or inorganic molecules.

Other compounds which can be screened in accordance with the invention include, but are not limited to small organic molecules that are able to gain entry into an appropriate cell (e.g. an endothelial cell) and affect the expression of a Bv8 gene or some other gene involved in a Bv8 mediated pathway (e.g., by interacting with the regulatory region or transcription factors involved in gene expression); or such compounds that affect or substitute for the activity of the Bv8 or the activity of some other intracellular factor involved in a Bv8 signal transduction, catabolic, or metabolic pathways.

Computer modeling and searching technologies permit identification of compounds, or the improvement of already identified compounds, that can modulate Bv8 expression or activity. Having identified such a compound or composition, the active sites or regions are identified. Such active sites might typically be ligand binding sites.

The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intramolecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site (or binding site), either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential modulators of Bv8 activity.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites (or binding sites) of Bv8, and related transduction and transcription factors will be apparent to those of skill in the art.

Examples of molecular modeling systems are the CHARMm and QUANTA programs (Polygen Corporation, Waltham, Mass.). CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988, Acta Pharmaceutical Fennica 97:159-166; Ripka, New Scientist 54-57 (Jun. 16, 1988); McKinaly and Rossmann, 1989, Annu. Rev. Pharmacol. Toxiciol. 29:111-122; Perry and Davies, OSAR: Quantitative Structure-Activity Relationships in Drug Design pp. 189-193 (Alan R. Liss, Inc. 1989); Lewis and Dean, 1989 Proc. R. Soc. Lond. 236:125-140 and 141-162; and, with respect to a model receptor for nucleic acid components, Askew, et al., 1989, J. Am. Chem. Soc. 111:1082-1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Compounds identified via assays such as those described herein may be useful, for example, in elucidating the biological function of a Bv8 gene product. Such compounds can be administered to a patient at therapeutically effective doses to treat any of a variety of physiological disorders. A therapeutically effective dose refers to that amount of the compound sufficient to result in any amelioration, impediment, prevention, or alteration of any biological symptom.

b. Assays for Compounds that Bind to Bv8

Systems may be designed to identify compounds capable of interacting with (e.g., binding to) or mimicking Bv8, or capable of interfering with the binding of Bv8 to a cognate receptor, binding partner or substrate. The compounds identified can be useful, for example, in modulating the activity of wild type and/or mutant Bv8 gene products; can be useful in elaborating the biological function of Bv8; can be utilized in screens for identifying compounds that disrupt normal Bv8 interactions; or may themselves disrupt or activate such interactions.

The principle of the assays used to identify compounds that bind to Bv8, or Bv8 cognate receptors or substrates, involves preparing a reaction mixture of Bv8 and the test compound under conditions and for a time sufficient to allow the two components to interact and bind, thus forming a complex which can be removed and/or detected in the reaction mixture. The Bv8 species used can vary depending upon the goal of the screening assay. For example, where agonists of the natural receptor are desired, the full-length Bv8, or a soluble truncated Bv8, a peptide, or fusion protein containing one or more Bv8 domains fused to a protein or polypeptide that affords advantages in the assay system (e.g., labeling, isolation of the resulting complex, etc.) can be utilized. Where compounds that directly interact with Bv8 are sought, peptides corresponding to the Bv8 and fusion proteins containing Bv8 can be used.

The screening assays can be conducted in a variety of ways. For example, one method to conduct such an assay would involve anchoring the Bv8, polypeptide, peptide, or fusion protein therefrom, or the test substance onto a solid phase and detecting Bv8/test compound complexes anchored on the solid phase at the end of the reaction. In one embodiment of such a method, the Bv8 reactant may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for a Bv8 protein, polypeptide, peptide or fusion protein or the test compound to anchor any complexes formed in solution, and a labeled antibody specific for the other component of the possible complex to detect anchored complexes.

c. Assays for Compounds that Interfere with Bv8 Interactions

Macromolecules that interact with Bv8 are referred to, for purposes of this discussion, as "binding partners". These binding partners are likely to be involved in Bv8 mediated biological pathways. Therefore, it is desirable to identify compounds that interfere with or disrupt the interaction of such binding partners which may be useful in regulating or augmenting Bv8 activity in the body and/or controlling disorders associated with this activity (or a deficiency thereof).

The basic principle of the assay systems used to identify compounds that interfere with the interaction between Bv8 and a binding partner or partners involves preparing a reaction mixture containing Bv8, or some variant thereof, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the Bv8 and its binding partner. Control reaction mixtures are incubated without the test compound or with a placebo. The formation of any complexes between the Bv8 and the binding partner is then detected. The formation of a complex in the control reaction, but not in the reaction mixture containing the test compound, indicates that the compound interferes with the interaction of the Bv8 and the interactive binding partner. Additionally, complex formation within reaction mixtures containing the test compound and normal Bv8 protein may also be compared to complex formation within reaction mixtures containing the test compound and a mutant Bv8. This comparison may be important in those cases wherein it is desirable to identify compounds that specifically disrupt interactions of mutant, or mutated, Bv8 but not the normal proteins.

The assay for compounds that interfere with the interaction between Bv8 and binding partners can be conducted in a heterogeneous or homogeneous format. Heterogeneous assays involve anchoring either the Bv8, or the binding partner, onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance; i.e., by adding the test substance to the reaction mixture prior to, or simultaneously with, Bv8 and interactive binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either Bv8 or an interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the Bv8 or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of Bv8 and an interactive binding partner is prepared in which either the Bv8 or its binding partners is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances that disrupt the interaction can be identified.

In a particular embodiment, a Bv8 fusion can be prepared for immobilization. For example, Bv8, or a peptide fragment thereof, can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art and described above. This antibody can be labeled with the radioactive isotope $^{125}$I, for example, by methods routinely practiced in the art. In a heterogeneous assay, the fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between Bv8 and the interactive binding partner can be detected by measuring the amount of radioactivity that remains associated with the glutathione-agarose beads. A successful inhibition of the interaction by the test compound will result in a decrease in measured radioactivity.

Alternatively, the GST fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the interaction between Bv8 and the binding partner can be detected by adding the labeled antibody and measuring the radioactivity associated with the beads.

In another embodiment of the invention, these same techniques can be employed using peptide fragments that correspond to the binding domains of Bv8 and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensatory mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a relatively short, labeled peptide comprising the binding domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

For example, and not by way of limitation, Bv8 can be anchored to a solid material as described, above, by making a GST fusion protein and allowing it to bind to glutathione agarose beads. The interactive binding partner can be labeled with a radioactive isotope, such as $^{35}S$, and cleaved with a proteolytic enzyme such as trypsin. Cleavage products can then be added to the anchored fusion protein and allowed to bind. After washing away unbound peptides, labeled bound material, representing the intracellular binding partner binding domain, can be eluted, purified, and analyzed for amino acid sequence by well-known methods. Peptides so identified can be produced synthetically or fused to appropriate facilitative proteins using recombinant DNA technology.

6. Pharmaceutical Compositions

The Bv8 polypeptides and modulators thereof described herein may be employed as therapeutic agents. The Bv8 polypeptides and Bv8 modulators of the present invention can be formulated according to known methods to prepare pharmaceutically useful compositions, whereby the Bv8 product hereof is combined in admixture with a pharmaceutically acceptable carrier vehicle. Therapeutic formulations of Bv8 are prepared by mixing Bv8 having the desired degree of purity, preferably essentially pure, with optional physiologically acceptable carriers, excipients or stabilizers (Remington's Pharmaceutical Sciences, supra), in the form of lyophilized cake or aqueous solutions. Acceptable carriers, excipients or stabilizers are nontoxic to the cell or mammal being exposed at the dosages and concentrations employed. Examples include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN®, PLURONICS®, or PEG.

Bv8 to be used for in vivo administration must be sterile. This is readily accomplished by any method known in the art, such as filtration through sterile filtration membranes, prior to or following lyophilization and reconstitution. Bv8 may be stored in lyophilized form. Therapeutic Bv8 compositions generally are placed into a container having a sterile access port, for example, an intravenous solution bag or vial having a stopper pierceable by a hypodermic injection needle.

Bv8 optionally is combined with or administered in concert with other growth factors. For example, it may be combined with EG-VEGF or VEGF.

Bv8 may be used with other conventional therapies for treating cancer.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

Where sustained-release administration of a Bv8 polypeptide or modulator is desired in a formulation with release characteristics suitable for the treatment of any disease or disorder requiring administration of the Bv8 polypeptide, microencapsulation of the Bv8 polypeptide or modulator is contemplated. For example, Bv8 in purified form may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, 1980, (A. Osol, Ed).

Bv8 may be incorporated into sustained release preparations for therapeutic use. Suitable examples of sustained release preparations include semipermeable polymer matrices in the form of shaped articles, e.g. films, or microcapsules. Examples of sustained release matrices include polyesters, hydrogels (e.g. poly(2-hydroxyethyl-methacrylate) as described by Langer et al., *J. Biomed. Mater. Res.*, 15:167-277 (1981) and Langer, *Chem. Tech.*, 12:98-105 (1982) or poly(vinylalcohol)), polylactides (U.S. Pat. No. 3,773,919, EP 58,481), copolymers of L-glutamic acid and gamma ethyl-L-glutamate (Sidman, et al., *Biopolymers* 22:547 (1983)), non-degradable ethylene vinyl acetate (Langer, et al., supra) or degradable lactic acid-glycolic acid copolymers such as the Lupron Depot™, (injectable microspheres composed of lactic acid-glycoloic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulthydryl residues, lyophilizing from acidic solutions, controlling moisture content, using appropriate additives, and developing specific polymer matrix compositions.

Sustained release Bv8 compositions also include liposomally entrapped Bv8. Liposomes containing Bv8 are prepared by methods known in the art. (Epstein, et al, 1985, Proc. Natl. Acid. Sci. 82:3688; Hwang, et al., 1980, Proc. Natl. Acad. Sci. USA 77:4030; DE 3,218,121 A; EP 52322A; EP 36676A; EP 88046A; EP 143949A; EP 142641A; Japanese Pat. App. No. 83-118008; U.S. Pat. Nos. 4,485,045 and 4,544.545; and EP 102,324A). Ordinarily the liposomes are of the small (about 200-800 Angstroms) unilamelar type in which the lipid content is greater than about 30 mol. % cholesterol, the selected proportion being adjusted for the optimal Bv8 therapy.

When applied topically, Bv8 is suitably combined with other ingredients, such as carriers and/or adjuvants. There are no limitations on the nature of such other ingredients, except that they must be physiologically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, plasters, and bandages, preferably in liquid or semi-liquid form.

For obtaining a gel formulation, Bv8 formulated in a liquid composition may be mixed with an effective amount of a water-soluble polysaccharide or synthetic polymer such as PEG to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the Bv8 held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight PEGs to obtain the proper viscosity. For example, a mixture of a PEG of molecular weight 400-600 with one of molecular weight 1500 would be effective for this purpose when mixed in the proper ratio to obtain a paste.

The term "water soluble" as applied to the polysaccharides and PEGs is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water-soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2-5%, more preferably about 3%, of the gel and Bv8 is present in an amount of about 300-1000 mg per ml of gel.

Semipermeable, implantable membrane devices are useful as means for delivering drugs in certain circumstances. For example, cells that secrete Bv8, Bv8 variants, Bv8 chimeras or Bv8 agonists or antagonists can be encapsulated, and such devices can be implanted into a patient. Accordingly, also included is a method for preventing or treating cancer which comprises implanting cells that secrete Bv8, its agonists or antagonists as may be required for the particular condition, into the body of patients in need thereof. Finally, the present invention includes a device for preventing or treating cancer by implantation into a patient of an implant comprising a semipermeable membrane, and cells that secrete Bv8 (or its agonists or antagonists as may be required for the particular condition) encapsulated within said membrane and said membrane being permeable to Bv8 (or its agonists or antagonists) and impermeable to factors from the patient detrimental to the cells. The patient's own cells, transformed to produce Bv8 ex vivo, could be implanted directly into the patient, optionally without such encapsulation. The methodology for the membrane encapsulation of living cells is familiar to those of ordinary skill in the art, and the preparation of the encapsulated cells and their implantation into patients may be accomplished without undue experimentation.

The pharmaceutical composition comprising Bv8 or Bv8 agonist or antagonist is preferably located in a suitable container. The container is preferably accompanied by instructions detailing the appropriate use and dosage of the pharmaceutical composition. One skilled in the art will recognize that these instructions will vary depending upon the method of treatment.

7. Methods of Treatment

The therapeutic agents provided herein can be used in a number of treatments. The treatments include treating a mammal, preferably a human, with a condition associated with hormone producing tissue or endocrine glands and/or with a condition associated with excessive, unwanted or uncontrolled angiogenesis. In one aspect, Bv8 or a Bv8 agonist is administered to a mammal in need thereof in an amount effective to treat the condition. Bv8 can be administered in a polypeptide or nucleic acid form. Preferably, Bv8 or a Bv8 agonist is used when the condition is one that requires the survival of or an increase in the number of cells producing a particular hormone. Examples of such conditions include diabetes. Other conditions include those wherein it is desired to increase the number of, or enhance the survival of cells in the reproductive organs, such as cells in the testis. Other conditions includes those wherein it is desired to decrease the formation of new blood vessels. Examples of such conditions include tumors, such as testicular cancer.

Bv8 may be administered along with another compound or composition. In one embodiment the compound is VEGF or an agonist or antagonist thereof. Optionally, the compound may be a nucleic acid that encodes a polypeptide, such as VEGF.

In one embodiment, compounds such as those identified by the screening assays in section 4 and 5, above, may be used to modulate the level of Bv8 activity or expression. Specifically, compounds identified that are Bv8 agonists or that are able to stimulate the binding of Bv8 to its receptor may be useful for treatments wherein an increased level of Bv8 activity is desired. Similarly, compounds identified that are able to increase Bv8 gene expression may be useful for this type of treatment.

Preferably, Bv8 or an agonist or antagonist thereof is administered to an individual with a condition associated with hormone producing tissue or endocrine glands, preferably a condition that requires a decrease in the number of cells producing a particular hormone, a decrease in cell proliferation or a decrease in angiogenesis. For example, a method of regulating fertility in an individual is provided herein which comprises administering a Bv8 antagonist to an individual in an amount effective to regulate fertility. Bv8 antagonists can also be administered to treat cysts and other conditions associated with overproliferation in hormone producing tissues.

Steroid hormone-dependent disorders may also be addressed using compositions and methods of the present invention. Such disorders include lipoid congenital adrenal hyperplasia, infertility, sexual maturation, androgen-dependent tumors, precocious puberty, McCune-Albright syndrome, adrenal-hypoplasia congenita, or hypogonadotropic hypogonadism.

A specific condition which can be treated by the agents and compositions provided herein is cancer, in particular steroid-, e.g. androgen-dependent cancer. A preferred method of treating cancer as provided herein comprises administering a Bv8 antagonist to an individual with or at risk of having cancer in an amount effective to treat the cancer. In one embodiment, the cancer is of the testis.

In a further embodiment, a Bv8 antagonist is administered to a patient in combination with one or more chemotherapeutic agents, such as in the treatment of cancer. It is contemplated that Bv8 may be administered prior to, during or after treatment with the chemotherapeutic agent such that the therapeutic efficacy is increased.

Preferred chemotherapeutic agents include but are not limited to vincristine, cisplatin, methotrexate, 3'-azido-3'-deoxythymidine, taxanes (e.g. paclitaxel (TAXOL®, Bristol-Myers Squibb Oncology, Princeton, N.J.) and doxetaxel (TAXOTERE®, Rhône-Poulenc Rorer, Antony, France)) and/or anthracycline antibiotics. The manufacturers' instructions may be followed in determining the preparation and dosing schedules for such chemotherapeutic agents or they may be determined empirically by the skilled practitioner. Preparation and dosing schedules for such chemotherapy are also described in Chemotherapy Service Ed., M.C. Perry, Williams & Wilkins, Baltimore, Md. (1992).

It is understood that the methods of increasing cell proliferation and inhibiting cell proliferation can be performed in vivo or in vitro. In some cases, it may be desirable to add Bv8 to a cell sample in vitro so as to stimulate proliferation of a specific cell type. The Bv8 treated sample can then be used in screening assays or be transplanted into an individual in need of treatment or into an animal model.

An effective amount of Bv8 or a Bv8 agonist or antagonist to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer the Bv8 until a dosage is reached that achieves the desired effect. A typical daily dosage for systemic treatment may vary from about 10 ng/kg to up to 100 mg/kg of mammal body weight or more per day, preferably about 1 µg/kg/day to 10 mg/kg/day, depending upon the route of administration. It is anticipated that different formulations will be effective for different treatment compounds and different disorders, and that administration targeting one organ or tissue, for example, may necessitate delivery in a manner different from that to another organ or tissue.

As an alternative general proposition, the Bv8 is formulated and delivered to the target site or tissue at a dosage capable of establishing in the tissue a Bv8 level that is efficacious but not unduly toxic. This intra-tissue concentration should be maintained if possible by continuous infusion, sustained release, topical application, Bv8-expressing cell implant, or injection at empirically determined frequencies. The progress of this therapy is easily monitored by conventional assays.

The dosing regimen must be determined based on the individual circumstances. However, in a preferred embodiment, Bv8 or a Bv8 agonist or antagonist is administered every day, more preferably every other day and even more preferably at least two times a week. The treatment is preferably continued for six months, more preferably for one month and even more preferably for at least two weeks. One skilled in the art will appreciate that the exact dosing regimen must be determined by the therapist based on the individual circumstances.

Nucleic acid encoding a Bv8 polypeptide may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad. Sci. USA 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 (1993)). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The Bv8 sequences can also be used in methods of diagnosis. Overexpression of Bv8 may indicate a cyst or cancer in a reproductive organ. Moreover, a sample from a patient may be analyzed for mutated or disfunctional Bv8. Generally, such methods include comparing Bv8 expression in a sample from a patient to that of a control.

8. Articles of Manufacture

In another aspect, the invention contemplates an article of manufacture comprising materials useful for the treatment or prevention of a disease or disorder or for regulating fertility. The article of manufacture preferably comprises a container and a label or package insert on or associated with the container. Suitable containers include, for example, bottles, vials, syringes, etc. The containers may be formed from a variety of materials such as glass and plastic. The container holds a composition comprising Bv8 or an agonist or antagonist thereof and the label or package insert preferably provides instructions for using the Bv8 or agonist or antagonist thereof. In one embodiment, the article of manufacture comprises a Bv8 antagonist and instructions for using the Bv8 antagonist to treat or prevent cancer. In another embodiment the article of manufacture comprises Bv8 and instructions for using the Bv8 to treat or prevent a condition that is associated with hormone producing endothelial tissue. In yet another embodiment, the article of manufacture comprises a Bv8 antagonist and instructions for using the Bv8 antagonist to regulate fertility. The package insert indicates that the composition is to be administered in a dose of between about 0.01 µg/kg and 50 mg/kg.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

All references cited herein are hereby incorporated by reference.

Example 1

Northern Blot Analysis

To elucidate the expression pattern of Bv8, Northern blot analysis was performed using RNA from a wide variety of human, mouse and rat tissues. Human RNA blots were hybridized to a $^{32}$P-labelled DNA probe based on human Bv8 cDNA, while mouse and rat RNA blots were hybridized to a $^{32}$P-labelled DNA probe based on the murine Bv8 cDNA.

Northern blot analysis was performed according to methods well known in the art. For example, cDNA probes were prepared using 30-50 ng of the human or mouse cDNA fragments with the Redi-Prime II kit (Amersham), using $^{32}$P-dCTP 3000 uCi/mmol (Amersham). Probes were purified on Sephadex G50 spin columns (Pharmacia) and hybridization was carried out at 68° C. in ExpressHyb hybridization solution (Stratagene). In another example, blots were incubated with the probes in hybridization buffer (5×SSPE; 2×Denhardt's solution; 100 mg/mL denatured sheared salmon sperm DNA; 50% formamide; 2% SDS) for 60 hours at 42° C. The blots were washed several times in 2×SSC; 0.05% SDS for 1 hour at room temperature, followed by a 30 minute wash in 0.1×SSC; 0.1% SDS at 50° C. The blots were developed after overnight exposure by phosphorimager analysis (Fuji). Equivalent RNA loading was assessed by hybridization with a control actin probe.

Bv8 mRNA transcripts were detected. FIG. 9 shows that a single mRNA species of 1.8 kb was detected in human testis with a human Bv8 probe. No expression was detected in any of the other human tissues that were analyzed. FIG. 10A shows that a single mRNA species was detected in mouse testis and heart. FIG. 10B shows that 1.8 kb and 0.8 kb transcripts are present in rat testis but not in other rat tissues. Together, these findings indicate that the testis is the major site of expression of Bv8 mRNA.

Example 2

Cell Proliferation Assays

To determine the responsiveness of particular cell types to Bv8, bovine adrenal cortical capillary endothelial cells (ACE) and bovine brain capillary endothelial cells (BBC) were assayed for proliferative response.

Figure 11:
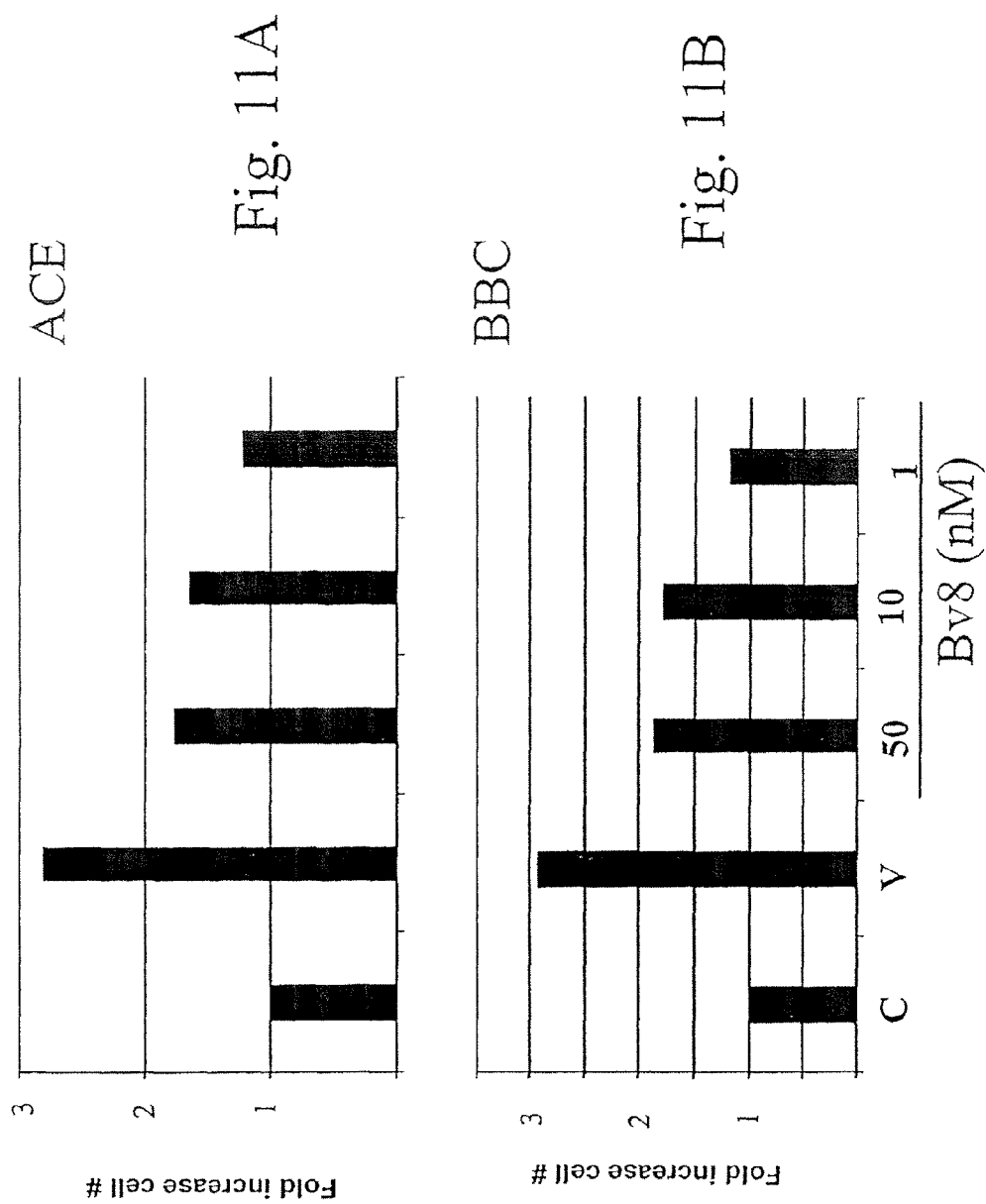
FIGS. 11A and 11B show that Bv8 induces proliferation of endothelial cells.

Briefly, ACE (adrenal cortical capillary endothelial cells) and BBC (bovine brain capillary) endothelial cells were cultured in low glucose DMEM supplemented with 10% bovine calf serum. For cell proliferation assays, 6000 cells were plated in each well of 12-well plates in the above media without any addition for control ("C" in FIG. 11), 10 ng/ml VEGF ("V" in FIG. 11), 50, 10 or 1 nM Bv8 (Fc-tagged recombinant protein). Total cell counts were obtained after 1 week using a Coulter counter. The fold-increase in cell number is relative to the control condition arbitrarily set to a value of 1. Media and other cell culture reagents were obtained from Life Technolgies, Inc. For the performance of the assay see also Aravind and Koonin, *Curr. Biol.* 8:477-478 (1998).

Preliminary results are shown in FIGS. 11A and 11B, which indicates the increase in number of cells relative to controls. Bv8 produced an increase in cell proliferation at all concentrations tested, with a maximal effect observed at a concentration of 50 nM. VEGF, a positive control, induced a nearly three-fold increase in proliferation of both ACE and BCC cells compared to the untreated control.

Example 3

Cell Survival Assay

The effect of Bv8 on the survival of endothelial cells was measured. Approximately 2×10⁵ bovine brain capillary (BBC) cells were plated in each well of E-well plates containing complete media (as descried in Example 2, above). The following day the complete media was aspirated and cells were cultured in media without any addition or in media comprising one of the following components: 2% FCS, 10% FCS, 20 ng/ml VEGF ("V" in FIG. 12), 5 nM Bv8, 25 mM Bv8, 20 ng/ml VEGF+25 nM Bv8 ("V+Bv8" in FIG. 12), or 25 nM EG-VEGF. After incubation for 48 hours, cells were removed by trypsinization and fixed in cold 70% ethanol for several hours. Cells were then stained at room temperature for 2-4 hours with 5 µg/ml propidium iodine and 20 ng/ml RNase in PBS. The sub-G1 profile of cells was determined by FACS analysis. This percentage of the cell population was plotted as percent apoptotic cells on the vertical axis of the graph in FIG. 12.

Figure 12:
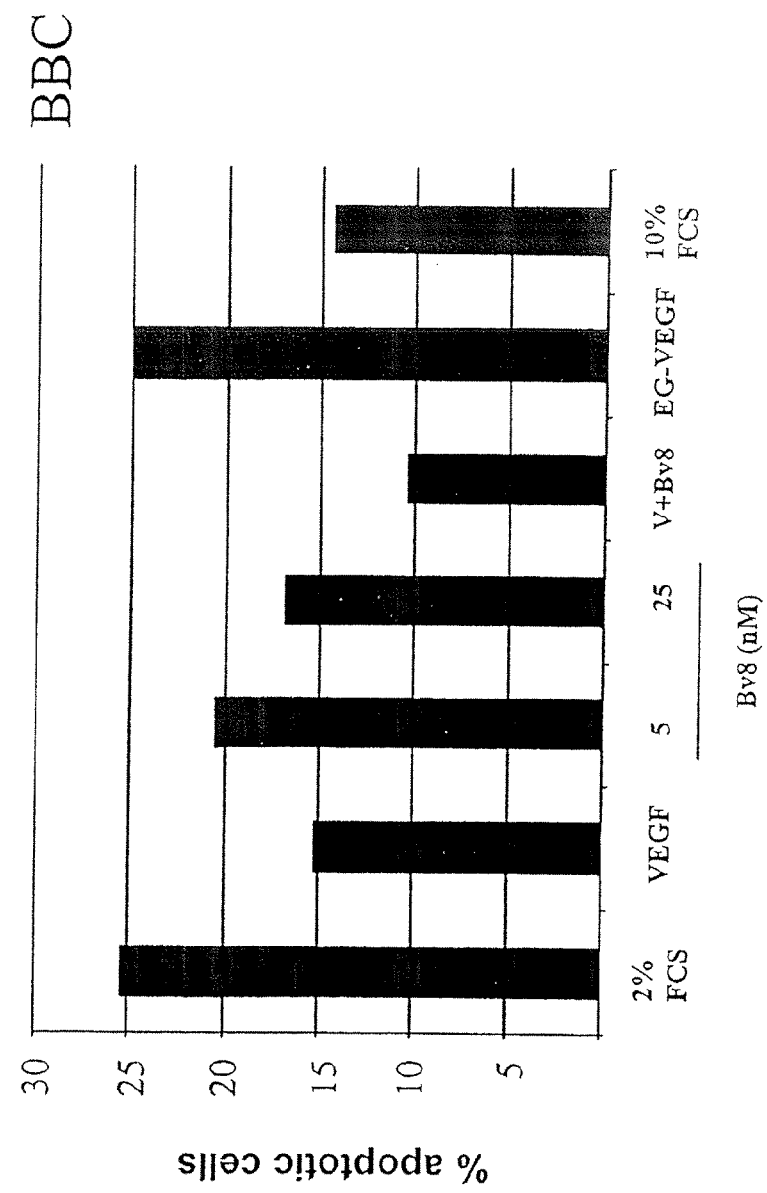
FIG. 12 shows that Bv8 promotes endothelial cell survival. Following incubation in media containing 5 or 25 nM Bv8, fewer bovine brain capillary cells were apoptotic than after incubation in 2% FCS or EG-VEGF. Bv8 and VEGF showed a synergistic effect, with fewer apoptotic cells present in culture following incubation with both Bv8 and VEGF than in either individually.

As can be seen in FIG. 12, Bv8 enhanced the survival of BBC endothelial cells. In particular, fewer apoptotic cells were visible in culture in the presence of either concentration of Bv8 than in the presence of 2% FCS or 25 nM EG-VEGF. Bv8 and VEGF showed a synergistic effect, with a combination of the two compounds increasing cell survival to a greater extent than either growth factor on its own or 10% FCS.

Example 4

In Vivo Induction of Angiogenesis

The ability of Bv8 to induce an angiogenic response was measured. In one set of experiments, the effect of Bv8 on the intratesticular vascular proliferation in the testis of Beige nude male mice was determined.

Adenovirus encoding LacZ, VEGF, and EG-VEGF have been previously described (LeCouter, Nature, 412: 877-84, 2001, incorporated herein by reference). For production of adenovirus encoding Bv8, cDNA encoding the mouse Bv8 81 amino acid isoform was cloned into the CMV shuttle vector (Stratagene) and the manufacturer's instructions were followed to produce recombinant adenovirus vector and recombinant virus. Virus was purified using the large-scale kit from Virapur (Carlsbad, Calif.), and titered.

For in vivo studies, adenoviral vectors (LacZ, VEGF, EG-VEGF and Bv8) were injected in the testis of Beige nude mice at 10⁷-10⁸ pfu (n=5). After seven days, animals were killed and the testes were fixed and processed for histology.

Figure 13:
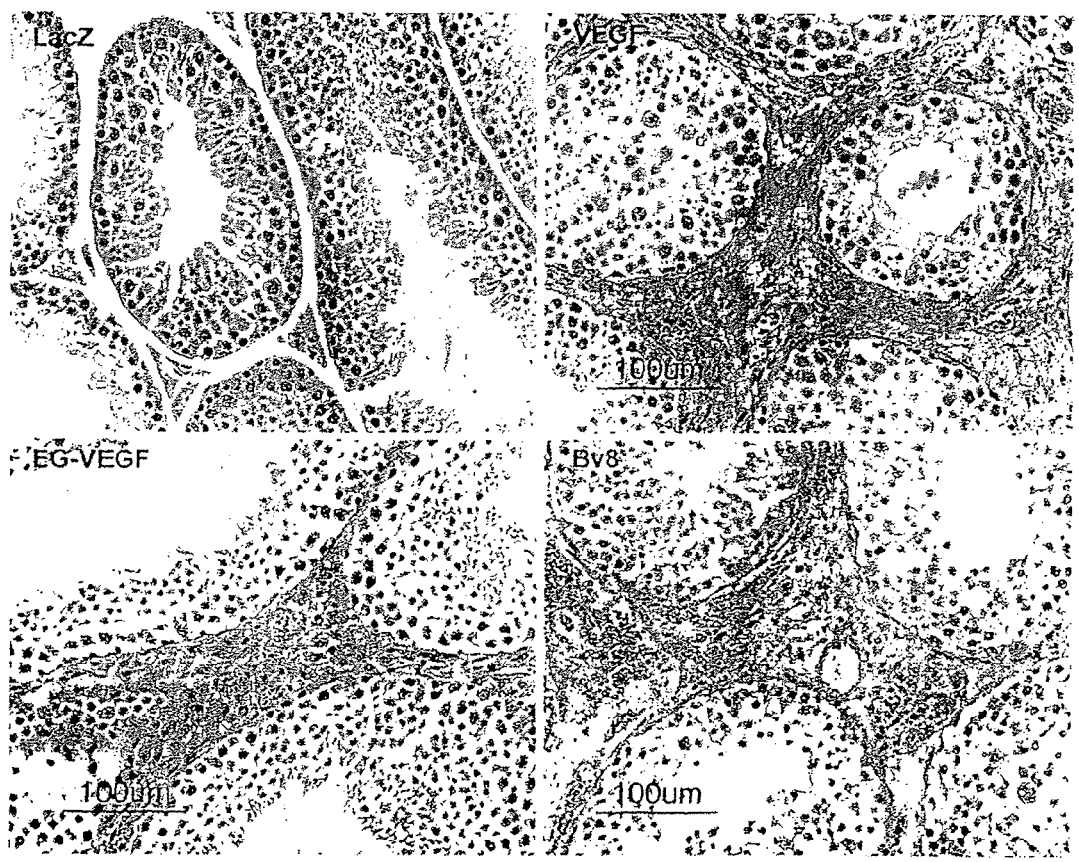
FIG. 13 shows that Bv8 increased interstitial capillary formation in the testis of nude mice. Following injection of testis of mice with adenoviral vectors, expressing either LacZ, VEGF, EG-VEGF, or Bv8, an increase in intratesticular vascular proliferation was observed in Bv8-treated animals.

As can be seen in FIG. 13, Bv8, similar to VEGF and EG-VEGF, increased in vivo interstitial capillary formation in testis cells of nude mice. No increase in interstitial capillary formation or angiogenesis was observed in either the PBS or LacZ adenovirus control groups. In a number of treated animals, tubular atrophy was also observed. The tubular atrophy may result from an increase in interstitial pressure that results from an induction of the angiogenic response.

The foregoing written specification is considered to be sufficient to enable one skilled in the art to practice the invention. However, various modifications of the invention in addition to those shown and described herein will be apparent to those skilled in the art from the foregoing description and fall within the scope of the appended claims.

Sequence CWU 1

6 1 427 DNA Homo sapiens 1 tgagggcgcc atgaggagcc tgtgctgcgc cccactcctg ctcctcttgc tgctgccgcc 60
gctgctgctc acgccccgcg ctggggacgc cgccgtgatc accggggctt gtgacaagga 120
ctcccaatgt ggtgcaggca tgtgctgtgc tgtcagtatc tgggtcaaga gcataaggat 180
ttgcacacct atgggcaaac tgggagacag ctgccatcca ctgactcgta aaaacaattt 240
tggaaatgga aggcaggaaa gaagaaagag gaagagaagc aaaaggaaaa aggaggttcc 300
attttttggg cggaggatgc 360
atcacacttg cccatgtctg ccaggcttgg cctgtttacg gacttcattt aaccgattta tttgtttagc ccaaaagtaa tcgctctgga gtagaaacca 420 aatgtga 427 2 129 PRT Homo sapiens 2 Met Arg Ser Leu Cys Cys Ala Pro Leu Leu Leu Leu Leu Leu Leu Pro 1 5 10 15 Pro Leu Leu Leu Thr Pro Arg Ala Gly Asp Ala Ala Val Ile Thr Gly 20 25 30 Ala Cys Asp Lys Asp Ser Gln Cys Gly Gly Gly Met Cys Cys Ala Val 35 40 45 Ser Ile Trp Val Lys Ser Ile Arg Ile Cys Thr Pro Met Gly Lys Leu 50 55 60 Gly Asp Ser Cys His Pro Leu Thr Arg Lys Asn Asn Phe Gly Asn Gly 65 70 75 80 Arg Gln Glu Arg Arg Lys Arg Lys Arg Ser Lys Arg Lys Lys Glu Val 85 90 95 Pro Phe Phe Gly Arg Arg Met His His Thr Cys Pro Cys Leu Pro Gly 100 105 110 Leu Ala Cys Leu Arg Thr Ser Phe Asn Arg Phe Ile Cys Leu Ala Gln 115 120 125 Lys 3 363 DNA Homo sapiens 3 gagggcgcca tgaggagcct gtgctgcgcc ccactcctgc tcctcttgct gctgccgccg 60
ctgctgctca cgccccgcgc tggggacgcc gccgtgatca ccggggcttg tgacaaggac 120
tcccaatgtg gtgcaggcat gtgctgtgct gtcagtatct gggtcaagag cataaggatt 180
tgcacaccta tgggcaaact gggagacagc tgccatccac tgactcgtaa agtccattt 240 tttgggcgga ggatgcatca cacttgccca tgtctgccag gcttgg cctgtttacg gact 300 tcatttaacc gatttatttg tttagcccaa aagtaatcgc tctggagtag aaaccaaatg 360 tga 363 4 108 PRT Homo sapiens 4 Met Arg Ser Leu Cys Cys Ala Pro Leu Leu Leu Leu Leu Leu Leu Pro 1 5 10 15 Pro Leu Leu Leu Thr Pro Arg Ala Gly Asp Ala Ala Val Ile Thr Gly 20 25 30 Ala Cys Asp Lys Asp Ser Gln Cys Gly Gly Gly Met Cys Cys Ala Val 35 40 45 Ser Ile Trp Val Lys Ser Ile Arg Ile Cys Thr Pro Met Gly Lys Leu 50 55 60 Gly Asp Ser Cys His Pro Leu Thr Arg Lys Val Pro Phe Phe Gly Arg 65 70 75 80 Arg Met His His Thr Cys Pro Cys Leu Pro Gly Leu Ala Cys Leu Arg 85 90 95 Thr Ser Phe Asn Arg Phe Ile Cys Leu Ala Gln Lys 100 105 5 1338 DNA Mus musculus 5 cggacgcgtg ggcgtcccct aaccgccacc gcgtccccgg gacgccatgg gggacccgcg 60
ctgtgccccg ctactgctac ttctgctgct accgctgctg ttcacaccgc ccgccgggga 120
tgccgcggtc atcaccgggg cttgcgacaa ggactctcag tgcggaggag gcatgtgctg 180
tgctgtcagt atctgggtta agagcataag gatctgcaca cctatgggcc 240
aagtgggcga cagctgccac ccctgactc ggaaagttcc attttgggg cggaggatgc accacacctg 300 ccctgcctg ccaggcttgg cgtgtttaag gacttcttc aaccggttta tttgcttggc 360
ccggaaatga tcactctgaa gtaggaactt gaaatgcgac cctccgctgc acaatgtccg 420
tcgagtctca cttgtaattg tggcaaacaa agaatactcc agaaagaaat gttctccccc 480
ttccttgact ttccaagtaa cgtttctatc tttgattttt gaagtggctt tttttttttt 540 tttttttcc tttccttgaa ggaaagtttt gattttgga gagatttata gaggacttc 600 tgacatggct tctcatttcc ctgtttatgt tttgccttga catttttgaa tgccaataac 660
aactgttttc acaaatagga gaataagagg gaacaatctg ttgcagaaac ttccttttgc 720
cctttgcccc actcgccccg ccccgccccg ccccgcctg cccatgcgca gacagacaca 780
cccttactct tcaaagactc tgatgatcct caccttactg tagcattgtg ggttttctaca 840 cttccccgcc ttgctggtgg acccactgag gaggctcaga gagctagcac tgtacaggtt 900
tgaaccagat ccccaagca gctcatttgg ggcagacgtt gggagcgctc cag 960 gaactttt cctgcaccca tctggcccac tggctttcag ttctgctgtt taactggtgg 1020
gaggacaaaa ttaacgggac cctgaaggaa cctgccccgt ttatctagat ttgtttaagt aaaagacatt 1080
ttctccttgt tgtgaaatat tacatgtctt ttctttttt atctgaagct ttttttttt 1140 ttcttttaagt cttcttgttg gagacatttt aaagaacgca actcgaggaa gcattgattt 1200
tcatytggca tgacaggagt catcatttta aaaaatcggt gttaagttat aatttaaact 1260
ttatttgtaa cccaaaggty taatgtaaat ggattcctg atatcctgcc atttgtactg 1320
gtatcaatat ttytatgt 1338 6 107 PRT Mus musculus 6 Met Gly Asp Pro Arg Cys Ala Pro Leu Leu Leu Leu Leu Leu Leu Pro 1 5 10 15 Leu Leu Phe Thr Pro Pro Ala Gly Asp Ala Ala Val Ile Thr Gly Ala 20 25 30 Cys Asp Lys Asp Ser Gln Cys Gly Gly Gly Met Cys Cys Ala Val Ser 35 40 45 Ile Trp Val Lys Ser Ile Arg Ile Cys Thr Pro Met Gly Gln Val Gly 50 55 60 Asp Ser Cys His Pro Leu Thr Arg Lys Val Pro Phe Trp Gly Arg Arg 65 70 75 80 Met His His Thr Cys Pro Cys Leu Pro Gly Leu Ala Cys Leu Arg Thr 85 90 95 Ser Phe Asn Arg Phe Ile Cys Leu Ala Arg Lys 100 105

---

What is claimed is:

1. A method of inducing angiogenesis comprising contacting endothelial cells expressing Bv8 receptor with a polypeptide comprising the amino acid sequence of SEQ ID NO:2.

2. The method of claim 1 wherein said endothelial cells are in a steroidogenic tissue, wherein said steroidogenic tissue is selected from the group consisting of adrenal gland tissue, reproductive tissue, gut tissue, and respiratory tract tissue.

3. The method of claim 2, wherein the reproductive tissue comprises ovarian, testicular, uterine, or cervical tissue.

4. A method of inducing angiogenesis comprising contacting endothelial cells expressing Bv8 receptor with a polypeptide comprising the amino acid sequence of SEQ ID NO:4 in an amount effective to induce angiogenesis.

5. The method of claim 4 wherein said endothelial cells are in a steroidogenic tissue, wherein said steroidogenic tissue is selected from the group consisting of adrenal gland tissue, reproductive tissue, gut tissue, and respiratory tract tissue.

6. The method of claim 5, wherein the reproductive tissue comprises ovarian, testicular, uterine, or cervical tissue.

* * * * *